US011950348B2

(12) United States Patent
Moyer et al.

(10) Patent No.: US 11,950,348 B2
(45) Date of Patent: Apr. 2, 2024

(54) INDUCTION COIL ASSEMBLY FOR UTERINE ABLATION AND METHOD

(71) Applicant: AEGEA Medical Inc., Redwood City, CA (US)

(72) Inventors: Daniel Van Zandt Moyer, Redwood City, CA (US); Uriel Hiram Chee, Santa Cruz, CA (US); Torrey Pine Smith, Redwood City, CA (US); Hugh Edward Magen, Belmont, CA (US); Darin Charles Gittings, Sunnyvale, CA (US)

(73) Assignee: Aegea Medical Inc., Menlo Park, CA (US)

( * ) Notice: Subject to any disclaimer, the term of this patent is extended or adjusted under 35 U.S.C. 154(b) by 1139 days.

(21) Appl. No.: 16/721,560

(22) Filed: Dec. 19, 2019

(65) Prior Publication Data
US 2020/0128632 A1 Apr. 23, 2020

Related U.S. Application Data

(63) Continuation of application No. PCT/US2018/038626, filed on Jun. 20, 2018.
(Continued)

(51) Int. Cl.
*H05B 6/42* (2006.01)
*A61B 17/42* (2006.01)
(Continued)

(52) U.S. Cl.
CPC ............... *H05B 6/42* (2013.01); *A61B 17/42* (2013.01); *A61B 18/08* (2013.01); *A61B 18/12* (2013.01);
(Continued)

(58) Field of Classification Search
CPC ......... A61B 17/42; A61B 18/04; A61B 18/08; A61B 18/12; A61B 2017/4216;
(Continued)

(56) References Cited

U.S. PATENT DOCUMENTS 4,807,620 A 2/1989 Strul et al.
4,977,897 A 12/1990 Hurwitz
(Continued)

FOREIGN PATENT DOCUMENTS

CN 2679162 2/2005
CN 103619275 3/2014
(Continued)

OTHER PUBLICATIONS

The Supplementary European Search Report for Application No. EP 18 82 0442, dated Mar. 9, 2021.
(Continued)

*Primary Examiner* — Quang T Van
(74) *Attorney, Agent, or Firm* — Fish & Richardson P.C.

(57) ABSTRACT

A vapor delivery device includes an induction coil system. The induction coil system can include a coiled fluid tube, a coiled wire, a capsule between the coiled fluid tube and the wire, and a cooling fluid supply configured to force a cooling fluid through the capsule across the coiled wire. The induction coil system can include a closed loop ferrite core, a wire coiled around a first portion of the ferrite core, and a fluid tube coiled around a second portion of the ferrite core. A wire coil can be contained in a cartridge system removably coupleable to a disposable vapor delivery device. The system can include a fluid flow controller and induction power regulation to maintain a specific operating pressure range for vapor within a uterus or other bodily cavity, tract, or duct.

20 Claims, 31 Drawing Sheets

Related U.S. Application Data

(60) Provisional application No. 62/642,245, filed on Mar. 13, 2018, provisional application No. 62/524,041, filed on Jun. 23, 2017, provisional application No. 62/522,091, filed on Jun. 20, 2017.

(51) Int. Cl.
| | |
|---|---|
| *A61B 18/08* | (2006.01) |
| *A61B 18/12* | (2006.01) |
| *H01F 27/10* | (2006.01) |
| *H05B 6/02* | (2006.01) |
| *H05B 6/06* | (2006.01) |
| *H05B 6/10* | (2006.01) |
| *A61B 18/00* | (2006.01) |
| *A61B 18/04* | (2006.01) |
| *A61B 18/06* | (2006.01) |
| *H01F 27/28* | (2006.01) |

(52) U.S. Cl.
CPC .............. *H01F 27/10* (2013.01); *H05B 6/02* (2013.01); *H05B 6/06* (2013.01); *H05B 6/108* (2013.01); *A61B 2017/4216* (2013.01); *A61B 2018/00011* (2013.01); *A61B 2018/00559* (2013.01); *A61B 2018/00577* (2013.01); *A61B 2018/00744* (2013.01); *A61B 2018/00791* (2013.01); *A61B 2018/044* (2013.01); *A61B 2018/064* (2013.01); *H01F 27/2823* (2013.01)

(58) Field of Classification Search
CPC ........... A61B 2018/00011; A61B 2018/00559; A61B 2018/00577; A61B 2018/00744; A61B 2018/00791; A61B 2018/044; A61B 2018/048; A61B 2018/064; A61B 2090/064; A61B 2090/0803; A61K 38/00; C07D 207/16; C07D 277/06; C07K 5/0222; G06F 21/316; G06F 21/32; G06V 40/18; G06V 40/19; G06V 40/197; G06V 40/20; G06V 40/45; H01F 27/10; H01F 27/2823; H05B 6/02; H05B 6/06; H05B 6/108; H05B 6/42
USPC ....... 219/628, 629, 630, 631, 632, 667, 672, 219/674
See application file for complete search history.

(56) References Cited

U.S. PATENT DOCUMENTS

| | | | |
|---|---|---|---|
| 5,098,429 A | 3/1992 | Sterzer | |
| 5,277,201 A | 1/1994 | Stern | |
| 5,376,912 A | 12/1994 | Casagrande | |
| 5,585,766 A | 12/1996 | Shel | |
| 5,769,880 A | 6/1998 | Truckai et al. | |
| 5,976,129 A | 11/1999 | Desai | |
| 6,066,132 A | 5/2000 | Chen et al. | |
| 6,113,594 A | 9/2000 | Savage | |
| 6,425,867 B1 | 7/2002 | Vaezy et al. | |
| 6,425,877 B1 | 7/2002 | Edwards | |
| 6,451,012 B2 | 9/2002 | Dobak, III | |
| 6,465,765 B2 * | 10/2002 | Katayama | H05B 6/108 |
| | | | 219/629 |
| 6,554,780 B1 | 4/2003 | Sampson et al. | |
| 6,566,636 B1 | 5/2003 | Bentley et al. | |
| 6,681,998 B2 | 1/2004 | Sharpe et al. | |
| 6,692,490 B1 | 2/2004 | Edwards | |
| 6,743,184 B2 | 6/2004 | Sampson et al. | |
| 6,743,197 B1 | 6/2004 | Edwards | |
| 6,872,183 B2 | 3/2005 | Sampson et al. | |
| 6,906,296 B2 | 6/2005 | Centanni et al. | |
| 7,022,105 B1 | 4/2006 | Edwards | |
| 7,063,670 B2 | 6/2006 | Sampson et al. | |
| 7,326,235 B2 | 2/2008 | Edwards |
| 7,331,957 B2 | 2/2008 | Woloszko et al. |
| 7,512,445 B2 | 3/2009 | Truckai et al. |
| 7,717,909 B2 | 5/2010 | Strul et al. |
| 7,846,160 B2 | 12/2010 | Payne et al. |
| 8,025,656 B2 | 9/2011 | Gruber et al. |
| 8,221,401 B2 | 7/2012 | Sharkey et al. |
| 8,226,645 B2 | 7/2012 | Harrington et al. |
| 8,343,078 B2 | 1/2013 | Toth |
| 8,394,037 B2 | 3/2013 | Toth |
| 8,486,060 B2 | 7/2013 | Kotmel et al. |
| 8,500,732 B2 | 8/2013 | Truckai et al. |
| 8,506,563 B2 | 8/2013 | Truckai et al. |
| 8,529,562 B2 | 9/2013 | Vissy et al. |
| 8,540,708 B2 | 9/2013 | Truckai et al. |
| 8,551,082 B2 | 10/2013 | Strul et al. |
| 8,597,289 B2 | 12/2013 | Layton, Jr. et al. |
| 8,647,349 B2 | 2/2014 | Gruber et al. |
| 8,690,873 B2 | 4/2014 | Truckai et al. |
| 8,715,278 B2 | 5/2014 | Toth et al. |
| 8,721,632 B2 | 5/2014 | Hoey et al. |
| 8,814,796 B2 | 8/2014 | Martin et al. |
| 8,840,625 B2 | 9/2014 | Adams et al. |
| 8,926,629 B2 | 1/2015 | Truckai |
| 8,936,592 B2 | 1/2015 | Beck et al. |
| 8,939,971 B2 | 1/2015 | Truckai et al. |
| 8,956,348 B2 | 2/2015 | Bek |
| 8,998,898 B2 | 4/2015 | Truckai et al. |
| 8,998,901 B2 | 4/2015 | Truckai et al. |
| 9,050,102 B2 | 6/2015 | Truckai |
| 9,050,103 B2 | 6/2015 | Truckai |
| 9,060,761 B2 | 6/2015 | Hastings et al. |
| 9,095,348 B2 | 8/2015 | Truckai et al. |
| 9,144,421 B1 | 9/2015 | Lau et al. |
| 9,149,321 B2 | 10/2015 | Stringham et al. |
| 9,186,208 B2 | 11/2015 | Truckai et al. |
| 9,204,889 B2 | 12/2015 | Shadduck |
| 9,242,122 B2 | 1/2016 | Tsoref et al. |
| 9,247,989 B2 | 2/2016 | Truckai |
| 9,259,262 B2 | 2/2016 | Hundertmark et al. |
| 9,277,952 B2 | 3/2016 | Burnett et al. |
| 9,283,022 B2 | 3/2016 | Burnett et al. |
| 9,289,257 B2 | 3/2016 | Toth et al. |
| 9,320,560 B2 | 4/2016 | Manwaring et al. |
| 9,333,111 B2 | 5/2016 | Kochem et al. |
| 9,339,330 B2 | 5/2016 | Truckai |
| 9,408,657 B2 | 8/2016 | Burnett et al. |
| 9,421,059 B2 | 8/2016 | Truckai et al. |
| 9,427,556 B2 | 8/2016 | Burnett |
| 9,433,467 B2 | 9/2016 | Beck et al. |
| 9,486,267 B2 | 11/2016 | Burnett et al. |
| 9,498,274 B2 | 11/2016 | Burnett et al. |
| 9,526,555 B2 | 12/2016 | Hoey et al. |
| 9,554,853 B2 | 1/2017 | Strul et al. |
| 9,561,067 B2 | 2/2017 | Sharma |
| 9,585,712 B2 | 3/2017 | Truckai |
| 9,615,875 B2 | 4/2017 | Shadduck |
| 9,636,171 B2 | 5/2017 | Toth et al. |
| 9,662,060 B2 | 5/2017 | Peliks et al. |
| 9,662,163 B2 | 5/2017 | Toth et al. |
| 9,743,974 B2 | 8/2017 | Gurskis et al. |
| 9,743,978 B2 | 8/2017 | Skalyni |
| 9,775,542 B2 | 10/2017 | Toth |
| 9,788,890 B2 | 10/2017 | Toth et al. |
| 9,814,520 B2 | 11/2017 | Truckai |
| 9,848,933 B2 | 12/2017 | Burnett et al. |
| 9,883,907 B2 | 2/2018 | Toth et al. |
| 9,895,192 B2 | 2/2018 | Model |
| 9,913,681 B2 | 3/2018 | Beaudet |
| 9,993,290 B2 | 6/2018 | Chee et al. |
| 10,004,551 B2 | 6/2018 | Burnett et al. |
| 10,004,553 B2 | 6/2018 | Churchill et al. |
| 10,052,150 B2 | 8/2018 | Truckai et al. |
| 10,105,176 B2 | 10/2018 | Toth et al. |
| 10,179,019 B2 | 1/2019 | Chee et al. |
| 10,213,151 B2 | 2/2019 | Filloux et al. |
| 10,213,335 B2 | 2/2019 | Burnett et al. |
| 10,238,446 B2 | 3/2019 | Gurskis et al. |
| 10,299,856 B2 | 5/2019 | Chee et al. |

(56) References Cited

U.S. PATENT DOCUMENTS

| | | |
|---|---|---|
| 10,456,194 B2 | 10/2019 | Truckai |
| 10,499,981 B2 | 12/2019 | Model |
| 10,524,847 B2 | 1/2020 | Shadduck |
| 10,575,898 B2 | 3/2020 | Chee et al. |
| 10,588,689 B2 | 3/2020 | Truckai |
| 10,617,461 B2 | 4/2020 | Toth et al. |
| 10,624,694 B2 | 4/2020 | Kochem et al. |
| 10,722,298 B2 | 7/2020 | Skalnyi |
| 10,758,300 B2 | 9/2020 | Truckai et al. |
| 10,779,877 B2 | 9/2020 | Churchill et al. |
| 11,246,640 B2 | 2/2022 | Hoey et al. |
| 2002/0077645 A1 | 6/2002 | Wiener et al. |
| 2003/0230567 A1 | 12/2003 | Centanni et al. |
| 2004/0182855 A1 | 9/2004 | Centanni |
| 2005/0095168 A1 | 5/2005 | Centanni et al. |
| 2008/0021377 A1 | 1/2008 | Kienman et al. |
| 2008/0281318 A1 | 11/2008 | Herbette et al. |
| 2009/0054870 A1 | 2/2009 | Sharkey et al. |
| 2010/0094270 A1 | 4/2010 | Sharma |
| 2011/0118717 A1 | 5/2011 | Shadduck |
| 2012/0110824 A1 | 5/2012 | Smith et al. |
| 2012/0283724 A1 | 11/2012 | Toth et al. |
| 2013/0006231 A1 | 1/2013 | Sharma et al. |
| 2014/0276713 A1 | 9/2014 | Hoey et al. |
| 2015/0025515 A1 | 1/2015 | Hoey et al. |
| 2015/0126990 A1 | 5/2015 | Sharma et al. |
| 2016/0215753 A1 | 7/2016 | Westmoreland |
| 2016/0220296 A1 | 8/2016 | Hastings et al. |
| 2016/0227611 A1 | 8/2016 | Hatton et al. |
| 2016/0354140 A1 | 12/2016 | Sharma et al. |

FOREIGN PATENT DOCUMENTS

| | | | |
|---|---|---|---|
| CN | 104042338 | | 9/2014 |
| CN | 105615995 | | 6/2016 |
| JP | 2000241022 | | 9/2000 |
| JP | 2009277547 A | * | 11/2009 |
| WO | WO 2018/237091 | | 12/2018 |

OTHER PUBLICATIONS

Extended European Search Report in European Appln No. 23164653.0, dated Jul. 10, 2023, 10 pages.

* cited by examiner

INDUCTION COIL ASSEMBLY FOR UTERINE ABLATION AND METHOD

CROSS-REFERENCE TO RELATED APPLICATIONS

This application is a continuation of International Application No. PCT/US2018/038626, filed Jun. 20, 2018, which claims priority to U.S. Provisional Application Nos. 62/642,245, filed Mar. 13, 2018; 62/524,041, filed Jun. 23, 2017; and 62/522,091, filed Jun. 20, 2017, all of which are incorporated by reference herein in their entireties.

FIELD OF THE DISCLOSURE

The present disclosure relates to an induction coil and heating coil for producing vapor for ablating tissue in medical applications.

BACKGROUND

Various methods and systems for generating steam or vapor for tissue ablation for medical applications have been described. Some of these medical devices heat or vaporize water or saline, and deliver the heated or vaporized fluid to a target tissue site by use of a cannula, needle, or other delivery instrument. As a byproduct of heating the fluid, power supplied to these medical devices can generate heat in the device that can degrade performance of the induction coils or affect the handling of the device. Large insulation zones or air gaps can reduce the conduction of heat to the medical instrument, but add bulk and size to the delivery instrument which can be impactful for medical applications that require a lower profile delivery to the target tissue.

As the length of tissue treatment increases, the problem of heat accumulation becomes more acute. In many cases, short time durations or bursts of vapor treatment have been effective for causing thermal necrosis of tumors, fibroids, lesions of the lungs, prostate glands, and varicose veins. These short durations can last 3 to 20 seconds, which is sufficient time to provide thermal energy to ablate tissue at the depth appropriate for that particular application. For short time durations, the heat buildup in the inductive coil may be minimal.

Other thermal treatments require greater time durations to adequately ablate tissue to an effective depth. As a representative example, uterine endometrial ablation requires approximate two minutes of vapor delivery to effectively treat the uterine cavity to a depth of ablation of 3 to 6 mm. In such applications, heat mitigation can be an important design consideration.

SUMMARY

A hand held disposable device for treatment of abnormal uterine bleeding which incorporates an induction heating coil assembly that can reduce coil heating and power requirements in conjunction with a longer treatment cycle is disclosed. An active cooling mechanism to reduce heat buildup in the induction coil and reduce the size and bulk of the hand-held unit is described. The device can have a single-use heating element which contacts and heats water or saline, and a multi-use driving coil. The device can have a closed loop ferrite core to reduce excessive thermal buildup within the induction coil assembly.

A hand held disposable device for treatment of abnormal uterine bleeding which incorporates an induction heating coil to generate configured to deliver vapor within the device for ablation of tissue is described. The device can include a single-use heating element which contacts and heats water or saline, and a multi-use driving coil. Energy can be transferred inductively between the two coils. Treatment can be achieved by delivering vapor to the uterine cavity within a prescribed pressure range, typically about 50 mmHg, that is below the cracking pressure of the fallopian tubes, and for a period, typically about 2 minutes, that is long enough to achieve an ablation depth that reaches the myometrium.

The device can have a magnetic core to increase the inductance and magnetic coupling, for example, allowing flexibility to choose a frequency range that enables the induction coil configuration to be of an appropriate size that fits within the physical constraints of the handle of the medical device or delivery instrument, and to run at a higher efficiency that reduces the amount of active cooling needed.

The device can have a coaxial and/or concentrically aligned configuration of the heating coil and induction coil. The heating coils can be configured to run or be in loops. The heating coils can run or be positioned in a back and forth orientation, up and down along the induction coil to maximize the exposure to the magnetic field and vapor production time while maintaining a small profile.

For the magnetic core, material with a high magnetic permeability may be used to increase the efficiency and/or decrease the size of the induction heating arrangement. The magnetic material can help contain the magnetic flux, reducing electromagnetic interference to other components. The magnetic material may increase the magnetizing inductance, allowing efficient operation at lower frequencies. The magnetic material can increase coupling, thereby reducing the voltage and/or current necessary to drive a load at a certain power. Increased coupling may also allow efficient operation without needing to drive the arrangement at resonance, thereby significantly increasing the range of efficient driving frequency. If the arrangement is optionally driven in a resonant fashion, the higher inductance granted by the core can reduce the size of capacitors needed for resonance at a given frequency.

Because the magnetic material can increase the coil inductance, fewer turns of wire may be required. This may allow the use of a larger diameter wire without increasing the size of the induction coil configuration, subsequently reducing the ohmic heating losses. Litz wire may be appropriate for higher frequencies. The winding may be a single layer or it may be multiple layers thick to reduce the length of the arrangement as well as increase the inductance per turn.

The material may be chosen to have a high bulk resistivity (e.g. ferrite) to prevent current from circulating in the magnetic material. Alternatively, the magnetic material may be chosen to have a moderate or low resistivity and act as the heating element itself (e.g. mu metal or magnetic stainless steel).

The driving coil may be concentric with the heating coil/element (heating element is not necessarily a coil, but will be referred to as one here). In this case, the driving coil may be either the inner or outer coil. Alternatively, both coils may be around the magnetic material but not concentric with each other, as the magnetic material can conduct the magnetic flux between the two. This allows for arrangements where the coils are physically separated from each other to reduce heat conduction from the heating element to the driving coil, or to improve the physical mating operation between the two parts of the include an induction coil system. The location and position of the driving coil, comprising a coiled fluid tube and a coiled wire. The coiled fluid tube can be configured as a to carry a fluid, and the coiled wire can be configured to carry an electric current. The electric current in the coiled wire can generate a magnetizing inductance to inductively heat the coiled fluid tube. A capsule can separate item from the metallic tubes for heating. This can be done for cost saving purposes by allowing the driving coil to be configured as a re-usable or re-posable item versus a disposable component of the system. The location of the driving coil can also influence the efficiency of the electric field, the inductive heating of the metallic tube, the resultant heat buildup within the system, and the quality of the vapor that is produced. The driving coil can also be in a closed loop configuration with a ferrite core material, the coiled fluid tube, and the coiled wire. A cooling fluid supply can force a cooling fluid, such as air, through the capsule and across the coiled wire.

The magnetic material may take the form of a rod located concentrically with the driving coil and the heating element. The magnetic material may form a complete loop around both the driving coil and the heating coil to maximize coupling and magnetizing inductance. There may be one or more gaps in the magnetic material to reduce volume and/or prevent magnetic saturation of the material and reduce core losses. Gaps can be located near the middle of the driving coil to reduce their effect on coupling. Gaps may reduce the effect of mechanical tolerances where two pieces of magnetic material meet.

The induction coil assemblies described herein with and without active cooling can provide consistent vapor delivery for uterine endometrial ablation procedures without excessive thermal buildup and within the prescribed intrauterine pressure range.

A hand held disposable device configured to deliver vapor for ablation of tissue is described. The device can include an induction coil system, comprising a coiled fluid tube and a coiled wire. The coiled fluid tube can be configured to carry a fluid, and the coiled wire can be configured to carry an electric current. The electric current in the coiled wire can generate a magnetizing inductance to inductively heat the coiled fluid tube. A capsule can separate the coiled fluid tube and the coiled wire. A cooling fluid supply can force a cooling fluid, such as air, through the capsule and across the coiled wire.

The disposable device can have an induction coil system comprising a closed loop ferrite core. A wire configured to carry electric current can be coiled around a first portion of the closed loop ferrite core and at least partially surrounded by the closed loop ferrite core. A fluid tube configured to carry a fluid can be coiled around a second portion of the closed loop ferrite core and at least partially surrounded by the closed loop ferrite core. Electric current in the wire can generate a magnetizing inductance to inductively heat the fluid tube.

The disposable device can have a cartridge system coupleable to the disposable device. The cartridge system can include a connector configured to removable couple the cartridge system to the disposable vapor delivery device. The cartridge system can further include a wire coil configured to carry electric current, wherein the electric current in the wire produces a magnetic field in at least a portion of the coiled fluid tube when the cartridge system is coupled to the disposable vapor delivery device. A controller in the cartridge system can be configured to determine if the disposable vapor delivery device has previously been used. If the controller determines the device has not previously been used, the controller can provide the electric current to the wire coil.

DETAILED DESCRIPTION

Figure 1:
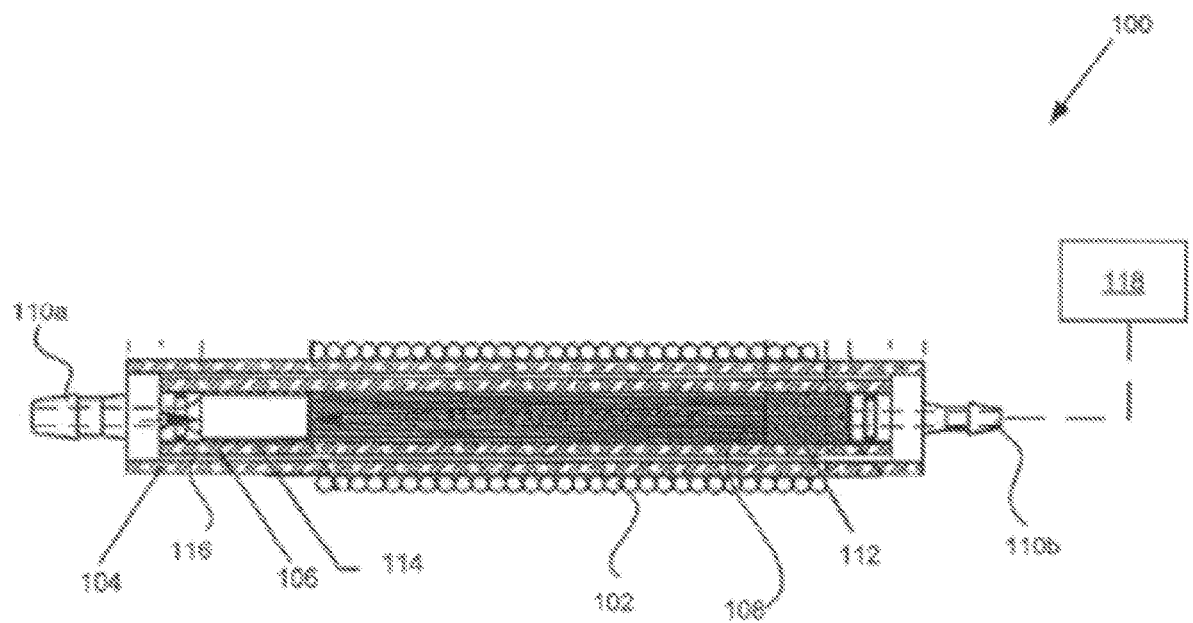
FIG. 1 illustrates an example induction coil.

FIG. 1 illustrates a cutaway view of an example induction coil 100 for a vapor generator. The vapor generator and system can supply thermal energy in vapor form to ablate tissue. Vapor can be used in the ablation of bodily cavities, vessels, or ducts in which the size, shape, and interior morphology can vary from patient to patient. Vapor is amorphous and can conform to contact the interior surface of the bodily cavity to effect ablation. One application is the ablation of endometrium for women with abnormal bleeding. Other applications include the gall bladder, or other cavities or lumens. The application for vapor can include tissue masses, tumors, or targeted tissue such as nerve, muscle, arterial, or venous vessels. The induction coil 100 can be configured to generate a high quality heated condensable vapor for any of these applications.

The vapor generator induction coil 100 can include an outer assembly 104 and an inner assembly 106 disposed within the outer assembly 104. The outer assembly 104 can be thermally insulating to reduce thermal damage to components of the induction coil 100 or transfer of excessive heat to an operator or patient. To thermally insulate the induction coil 100, the outer assembly 104 can comprise a material with a low thermal conductivity such as aerogel, foam, fiberglass, or low-density silicone. The outer assembly 104 can additionally or alternatively contain air gaps. In addition to being thermally insulating, the outer assembly 104 can be electrically insulating.

A wire 102 can be coiled around the outer assembly 104. The wire 102, which can comprise a Litz wire, an insulated wire, or a coiled magnet wire, can be coupled to an RF generator that can produce a current in the coiled wire 102 to generate an inductive electromagnetic field. The wire 102 can be wrapped around the outer assembly 104 for a specified number of turns or wraps. The number of wraps can depend on parameters of the application, including power requirements and gauge of the wire 102. The number of wraps can be low in number, for example 2, 3, or 4 complete (360 degree) wraps around the outer assembly 104, or can be higher numbers of wraps such as 30, 300, or 3000. The wire 102 can have a diameter between approximately 10 AWG and 20 AWG. For example, the outer assembly 104 can be wrapped by a wire 102 having a diameter of 16 AWG and approximately ten complete turns.

The inner assembly 106 can be electrically insulating and thermally conductive. For example, the inner assembly 106 can comprise a material such as aluminum nitride, alloys of iron including stainless steels, alloys of nickel including ferrite, alloys of cobalt, quartz, glass, or a ceramic such as aluminum oxide.

One or more metallic tubes 108 can be supported by the inner assembly 106. The tubes 108 can comprise a single tube that is wrapped around the inner assembly 106, and is also referred to herein as a "heating coil." The metallic tubes 108 can alternatively comprise an array of 10 tubes to 250 or more metallic microtubes, aligned in a parallel array. The one or more tubes 108 may have outside diameters ranging from 0.5 mm to 2.5 mm, and inside diameters in the range of 0.25 to 2 mm. The metallic tubes 108 can have magnetic permeability larger than 1.5 at the operating frequency of the generator. The tubes 108 may be bundled together, for example tightly enough so that there is physical contact between adjacent tubes 108. They may be physically joined with a metallic material such as solder, welds, mechanical joints, or the tubes may be holes drilled longitudinally through the length of a solid metallic rod.

The metallic tubes 108 can be coupled to a fluid source 118 supplying saline, water, distilled water, or other fluid to be heated or converted into steam or vapor in the tubes 108. The metallic tubes 108 and the fluid can be inductively heated by the inductive electromagnetic field generated by current in the coiled wire 102.

Figure 2:
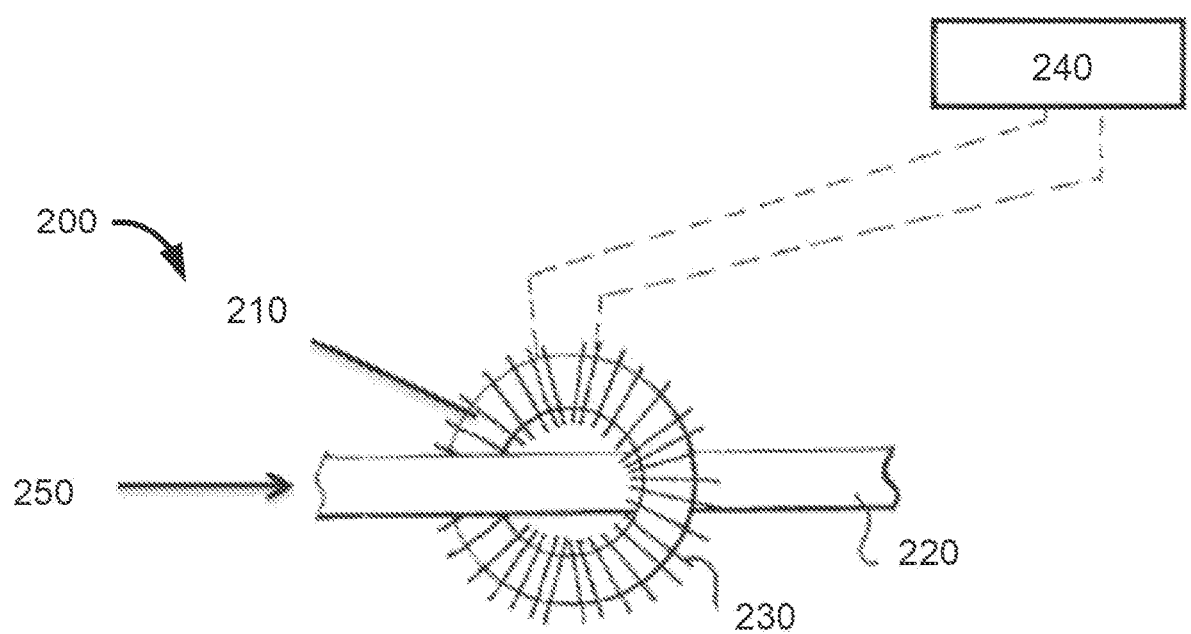
FIG. 2 illustrates an example closed loop induction coil.

FIG. 2 illustrates a closed loop ferrite induction coil system 200 that can be used to treat fluid within a pipe to reduce scaling in the fluid. The closed loop ferrite induction coil system 200 can include a closed loop ferrite ring 210 and a pipe 220. An insulated wire 230 can be wrapped around the closed loop ferrite ring 210 coupled to a RF power source 240, which can provide an alternating electrical current to create a magnetic field. Pipe 220 can contain fluid 250. The magnetic field generated by the current in the ferrite ring 210 can heat the pipe 220 and the fluid 250 by inductive heating. The closed loop ferrite assembly can reduce stray currents and thermal build up in the insulated wire 230 wrapping the ferrite ring 710.

Figure 3:
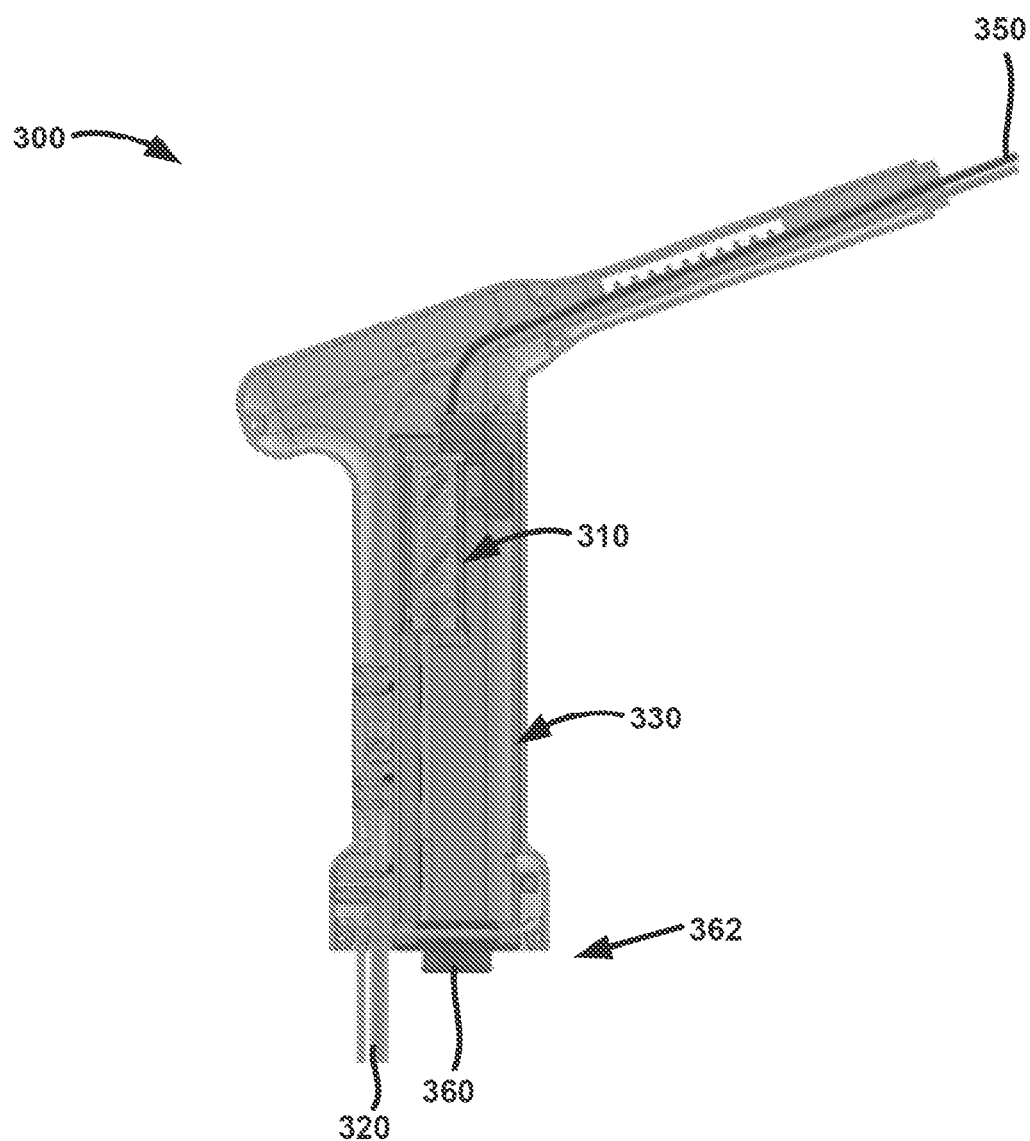
FIG. 3 illustrates a cut-away view of an example vapor delivery device.

FIG. 3 illustrates a cut-away view of an example vapor delivery device 300 including an induction coil assembly 310. The vapor delivery device 300 can be used, for example, for uterine endometrial ablation procedures. A user, such as a physician, can hold the vapor delivery device 300 by handle 330. Connections, conduits, and tubing to the controller and fluid supply (not shown in FIG. 3) can be provided through a connector 360 at the proximal end 362 of the vapor delivery device 300.

Figure 4A:
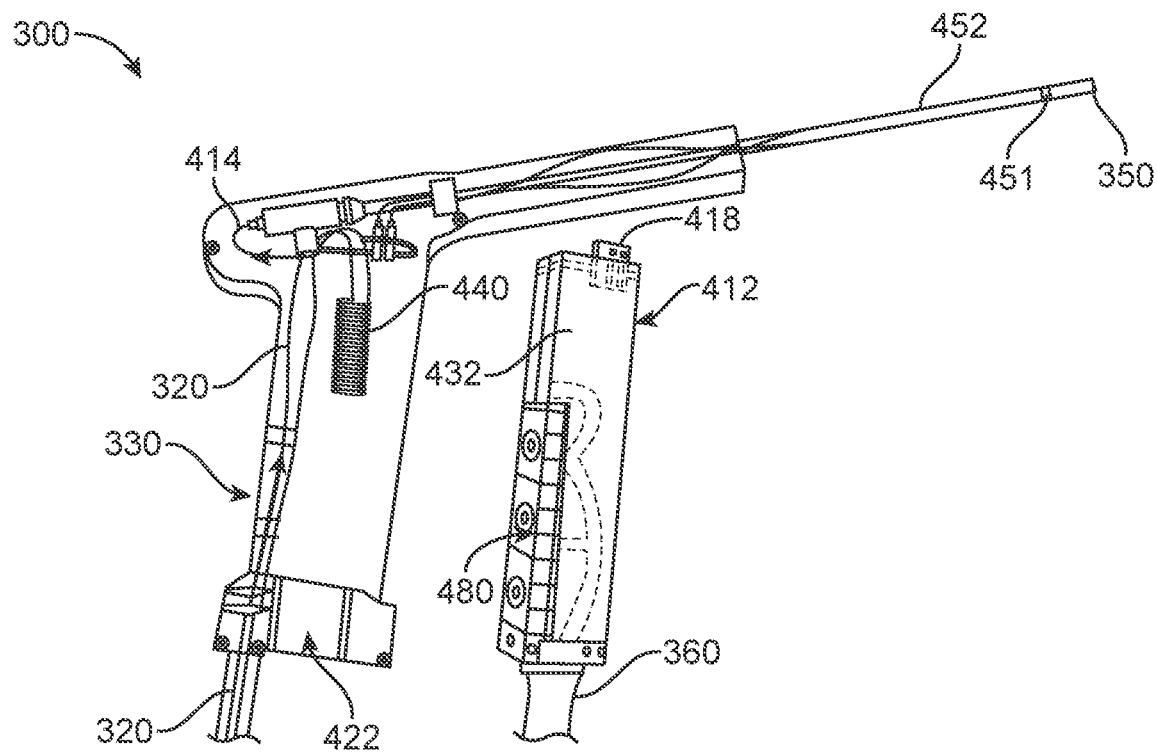
FIGS. 4a-4c illustrate an example vapor delivery device with a cartridge assembly.
Figure 4B:
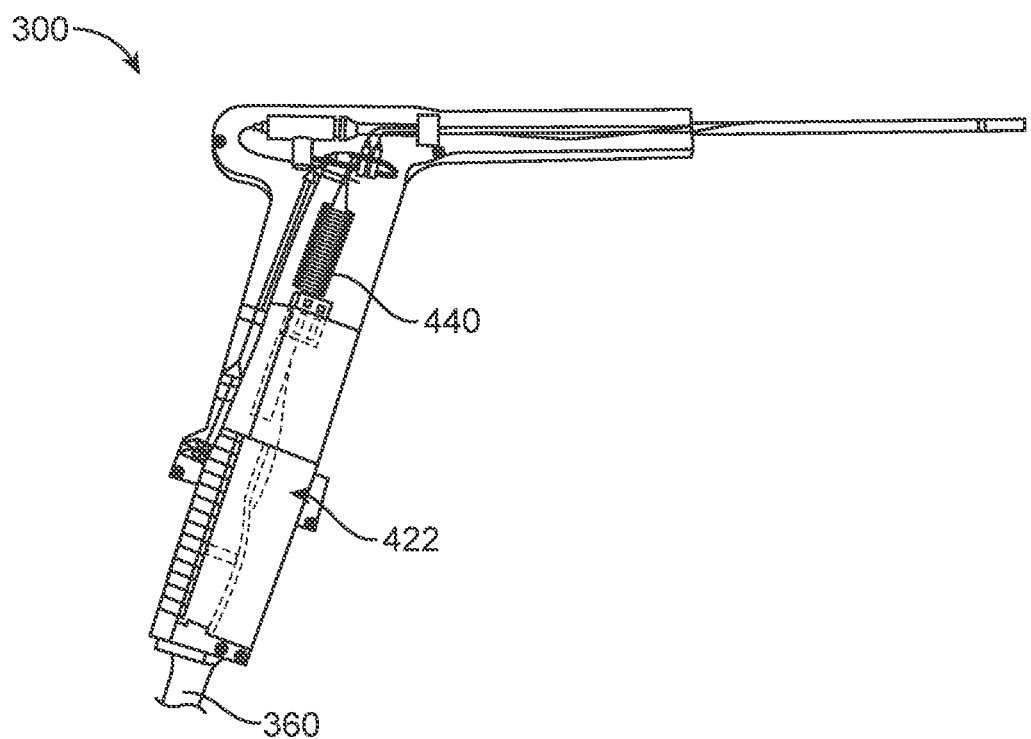
Figure 4C:
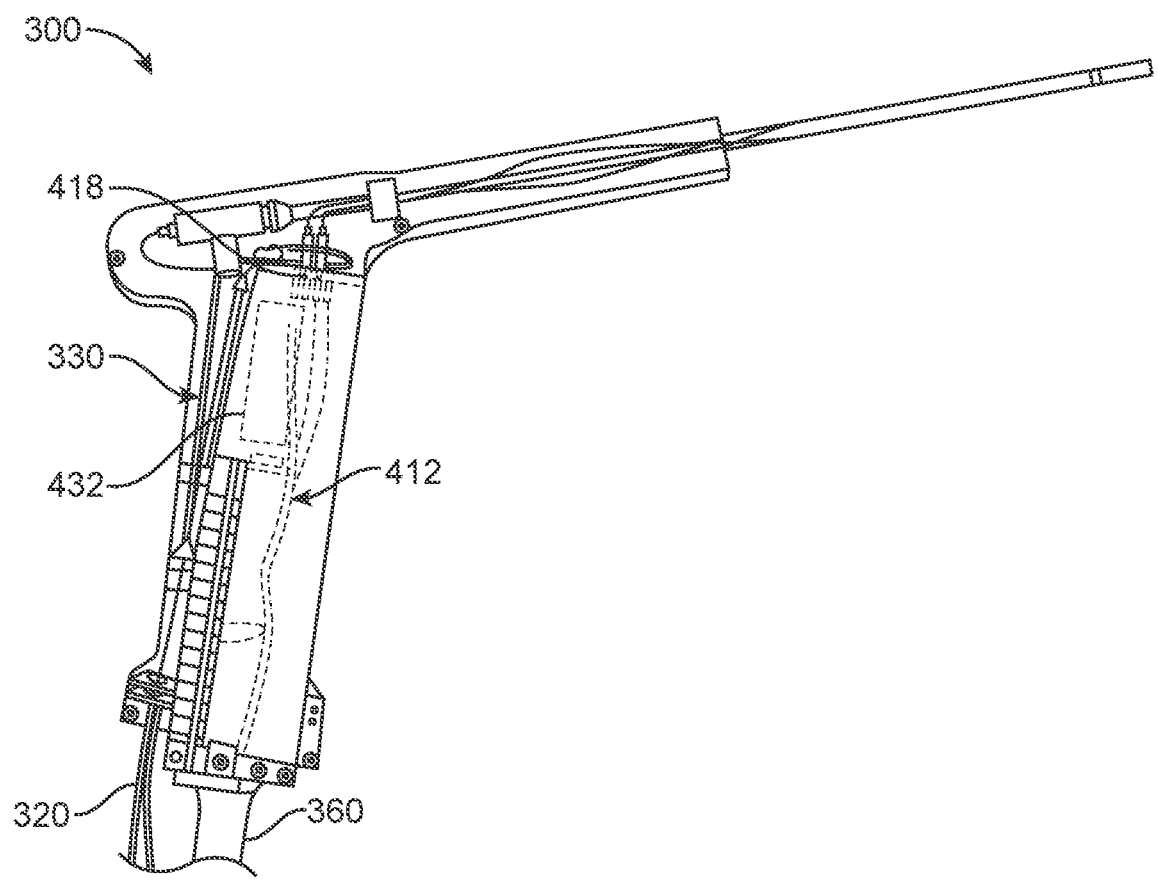

Fluid such as saline, water, or distilled water can be supplied to the vapor delivery device 300 through a fluid conduit 320. The induction coil assembly 310 can heat or vaporize the fluid entering the conduit 320. For example, the fluid can pass through the induction coil assembly 310, where a magnetic field generated by an alternating current in an insulated or Litz wire can heat or vaporize the fluid by inductive heating. The heated or vaporized fluid can be delivered through a distal end 350 to a target tissue site of the patient. Vapor delivery device can contain pressure sensors and pressure relief valves (not shown) to regulate the amount of vapor delivered to the bodily cavity FIGS. 4A through 4C show one example configuration of the vapor delivery device 300 and induction coil assembly 310. FIG. 4A shows one-half of the vapor delivery device 300 to illustrate the internal components of the device. The vapor delivery device 300 can have a handle 330 that can be manually grasped by the physician. At the proximal end of the handle 330 can be proximal opening 422 containing the fluid conduit 320. The distal end 350 of the vapor delivery device 300 can have an opening to provide vapor or heated fluid, or non-heated fluid or media to the target tissue site.

The fluid conduit 320 can provide a pathway for fluid to flow through the handle 330 and into the metallic tube 440. The fluid can be heated or vaporized in the metallic tube 440 when RF power is delivered, and the heated or vaporized fluid can enter the vapor input port 414 to be delivered to a target tissue site through distal end 350. Located near the distal end 350 of the vapor delivery device 300 can be a pressure sensor 451 and sealing balloons 452. The pressure sensor 451 can measure a pressure of a body cavity, such as an intrauterine pressure, and the sealing balloons 452 can interact with the endocervical canal once the distal end 350 has been inserted within the patient. For example, the sealing balloons 452 can inflate against the walls of the endocervical canal to stabilize the device and insulate. Air supply conduits within vapor delivery device provide pressurized air from an air supply source to inflate the sealing balloons 452 to occlude the endocervical canal.

Any fluid pathways that deliver fluid or vapor to the patient, as well as any portions of the device 300 that may contact the patient, can be contained in a disposable portion 470. A cartridge assembly 412, which can be a reusable or reposable instrument, can couple with the disposable portion 470 to form the vapor delivery device 300. The cartridge assembly 412 can include an inductive coil 432 that, together with the metallic tube 440, forms the induction coil assembly 310. When the cartridge assembly 412 is coupled to the disposable portion 470, current in the inductive coil 432 can inductively heat the metallic tube 440. For example, the cartridge assembly 412 can have an induction coil opening 418 that is designed to accept the metallic tube 440. When the cartridge assembly 412 is coupled with the disposable portion 470, the metallic tube 440 can fit within the induction coil opening 418 such that the metallic tube 440 at least partially overlaps the inductive coil 432 and resides within a magnetic field created by current in the inductive coil 432.

The cartridge assembly 412 can also include pneumatic valves 480, which can control fluid delivery for integrity tests or enhancing ultrasonic visualization of a bodily cavity. For example, the pneumatic valves 480 can aid in an integrity test to verify that a uterine cavity is intact and ready for ablation. A connection 360 can couple the cartridge assembly 412 to a controller (not shown). The connection 360 can contain an electrical connection for the inductive coil 432, air supply conduits for balloons 452, air cooling conduits to facilitate reducing excessive thermal effects within the handle 330 and the inductive coil 432, a connection for thermocouples for the inductive coil 432, a connection for a thermocouple in a portion of the vapor delivery device 300 that may contact a patient, a connection to pneumatic valves 480 that control fluid delivery for integrity tests to verify that the uterine cavity is intact and ready for vapor delivery, and/or a connection for the pressure sensor 451. These connections can couple corresponding components to the controller for processing, monitoring, and display by the controller hardware and software.

To use the vapor delivery device 300, a physician can insert the cartridge assembly 412 into the disposable portion 470. FIG. 4b demonstrates an example of the cartridge assembly 412 shown in FIG. 4a being inserted into vapor delivery device 300 but not yet fully coupled. In FIG. 4b, the cartridge assembly 412 can be inserted within proximal opening 422 of the handle 330 of the vapor delivery device 300.

FIG. 4c shows an example of the cartridge assembly 412 fully engaged within the vapor delivery device 300. Upon engagement, connections to thermocouples, intrauterine pressure sensors, electrical current from the controller, and air supply conduits can be completed. Fluid can then supplied through fluid conduit 320 to the metallic tube 440, where the fluid can be heated or vaporized when the induction coil 432 is powered and regulated via the controller.

The controller can also regulate vapor delivery to a target tissue site by the vapor delivery device 300. For the uterine endometrial ablation application, vapor delivery into the uterus can be monitored to avoid vapor escaping from the uterus via the fallopian tubes or the endocervical canal. As an example, high intrauterine vapor pressures can cause vapor to traverse the length of the fallopian tubes or cause thermal injury through the fallopian tube wall, potentially damage organs in the peritoneal cavity. The medical literature reports the average cracking pressure of fallopian tubes in women as 70 mmHg. The controller may therefore monitor the intrauterine pressure using the pressure sensors 451 and regulate the intrauterine pressure below 70 mmHg during the treatment procedure. In addition, the controller may monitor for sudden drops in intrauterine pressure or rapid increases in vapor flow, which may be indicative that a seal of endocervical canal has failed.

The controller can also monitor temperature of the inductive coil assembly 310. Excessive heat build-up can damage the inductive coil 432 or the vapor delivery device 300 itself. Excessive heat build-up can also create safety issues. For the operator, the inductive coil assembly 310 may be positioned in the handle held by the hand of the operator. For the patient, the vapor delivery device may be in close proximity to sensitive tissue, such as the patient's pelvic region, vagina, and cervix. In both situations, excessive heat build-up in the inductive coil assembly 310 can produce unintended thermal injury. Especially for procedures involving greater depths of ablation and large treatment areas, thermal build-up in the inductive coil assembly 310 can be problematic.

Active Air-Cooled Induction Coil System

To address heat build-up in the inductive coil assembly 310, the inductive coil assembly 310 can be insulated by foam, silicone, rubber, plastic, and/or air gaps. However, these layers of insulation and air gaps may lead to larger and heavier vapor delivery devices. For vapor delivery devices that are hand-held or designed to be used in a minimally invasive manner through a small portal into the patient's body, the size and weight of the device may significantly constrain its design. Accordingly, the vapor delivery device 300 may employ active cooling to provide for heat mitigation without a significant increase to the size or weight of the device.

Referring back to FIG. 4c, connection 360 can contain an air conduit that is designed to force air driven by an air pump in the controller (not shown) onto or into the inductive coil assembly 310. A portion of the heat generated in the inductive coil assembly 310 can be transferred to the air as it is forced past the Litz wire 432, cooling the inductive coil assembly 310. The data in Table 1 below and Graph 1 in FIG. 5 demonstrate the benefit of air cooling system on the inductive coil assembly.

TABLE 1

Airflow versus Wire Temperature in Inductive Coil Assembly
Steady state runs done at 95% vapor quality and 360 watts

| Air Flow (cfm) | Thermocouple 3 temperature |
|---|---|
| 0.5 | 149 |
| 0.66 | 138 |
| 0.83 | 132 |
| 1 | 118 |

Figure 5:
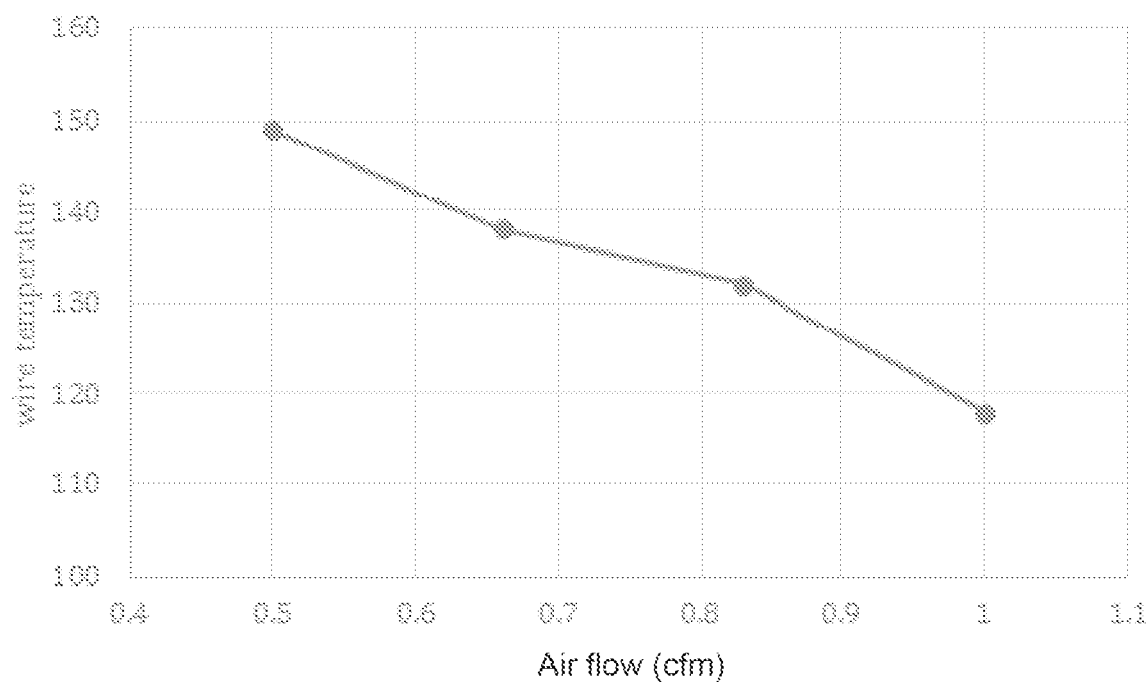
FIG. 5 is a graph illustrating an example relationship between wire temperature and air flow rate.

The data in Table 1 above and in Graph 1 in FIG. 5 illustrate a decrease in temperature of the Litz wire 432 corresponding to an increased rate of air flow. Accordingly, forcing air across the Litz wire 432 can beneficially mitigate heat build-up in the inductive coil assembly 310. The rate of air flow across the Litz wire 432 can be adjusted based on a desired wire temperature.

Figure 6:
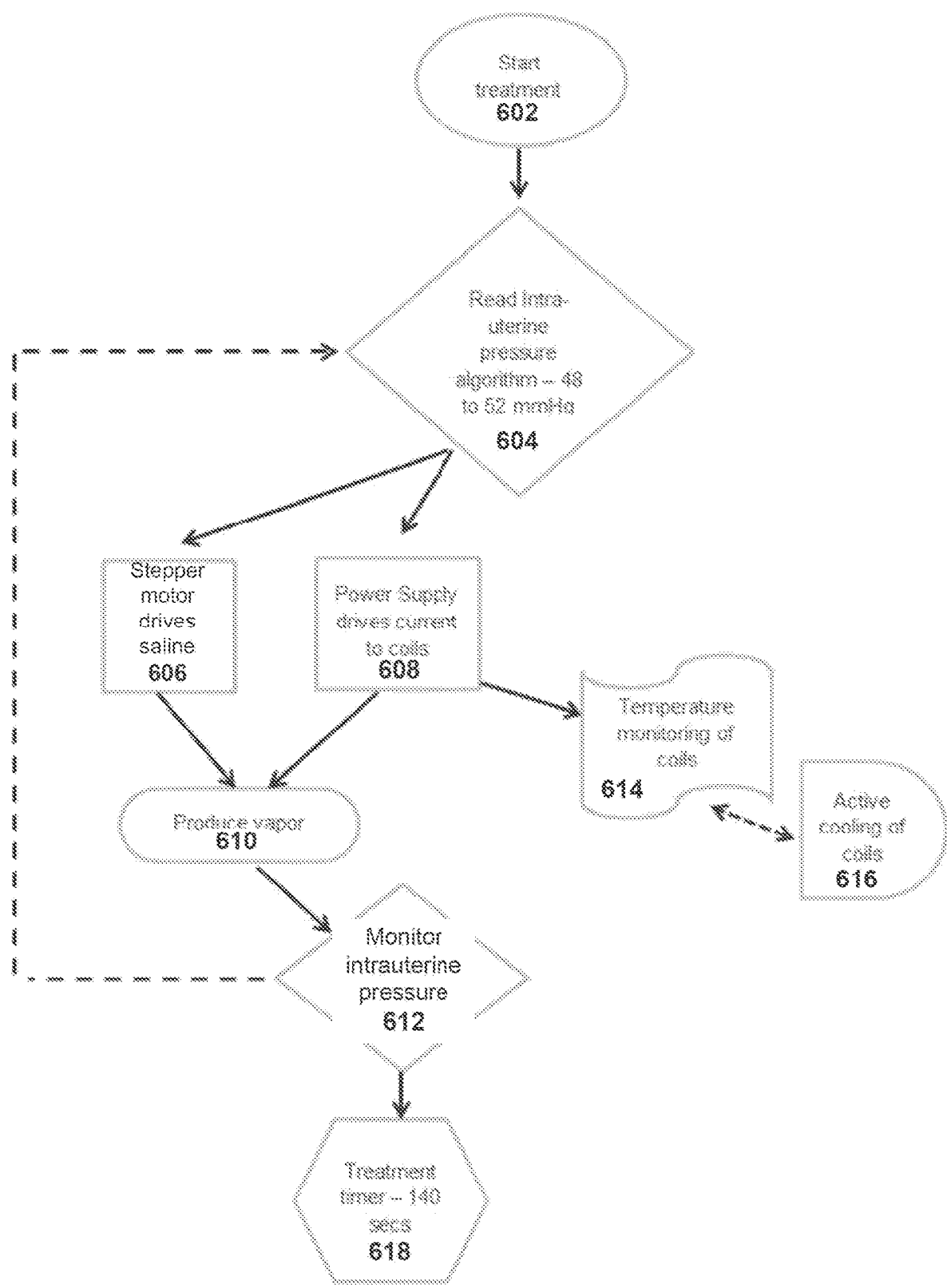
FIG. 6 is a flowchart illustrating an example algorithm for a pressure control system.

FIG. 6 illustrates an algorithm of a pressure control system for an inductive coil that can be used for vapor delivery in the uterine cavity. Once the vapor delivery device has had the required pre-procedure checks, endocervical sealing steps, safety tests, device insertion, and final device positioning and placement into the uterine cavity, the treatment can be ready to begin 602. Vapor can be produced by saline, water, or other fluid being driven into the metallic tube of the vapor delivery device 300. Simultaneously, or within a prescribed software and hardware driven fashion, electrical current from the RF power source can be provided to the inductive coil 432 in the inductive coil assembly 310. The resultant magnetic field can heat the metallic tube to heat the fluid. The flow of fluid into the metallic tube can be controlled by a stepper motor on a syringe pump, or a peristaltic pump, or other fluid flow or pressure controlled system. Within the vapor delivery device, an intrauterine pressure sensor 451 can monitor 604 the pressure of the vapor in the uterine cavity. A target range of intrauterine pressures can be between 20 to 60 mmHg, or 20 to 52 mmHg, or within a range of 48 to 52 mmHg. The pressure control system can be responsive to rapid changes in the intrauterine pressure. For example, the intrauterine pressure can change rapidly as a result of uterine contractions, condensation of the vapor, residual fluid, tissue, loose tissue, blood in the uterine cavity, and the outflow of fluid and material from the uterine cavity. The vapor delivery device can have in inflow of vapor at its distal end and an outflow conduit that can allow excess fluid, vapor, and uterine materials to exit out of the uterus as a continuous inflow/outflow system. The continuous inflow/outflow system provides for the continual inflow of vapor that can condense on the wall of the uterine cavity. However, this system and other systems used for other bodily cavities, lumens, or target tissues can have only a singular inflow port for the delivery of vapor.

Referring back to FIG. 6, the stepper motor can be controlled and monitored to drive 606 saline to the inductive coil assembly 310. The power supply can drive 608 current to the inductive coil 432 to heat the metallic tube 440 and produce 610 vapor. The resultant intrauterine pressure can be monitored 612 and feedback provided to the uterine cavity algorithm to maintain a targeted intrauterine pressure range between, e.g., 48 and 52 mmHg. During the treatment, the temperature of the inductive coil assembly can be monitored 614 to verify that a safe and proper operative range is maintained. The safe and proper temperature can be dynamically controlled by the active cooling 1232 of the inductive coil assembly. A temperature that exceeds or becomes outside the expected range can serve to produce an error condition that will terminate the vapor treatment procedure. In addition, thermocouples can be placed on one or both of the inductive coil 432 and the metallic tube 440 during the treatment cycle. Active cooling can also serve to regulate the temperature of the metallic tube 440 to facilitate control of the temperature of the inductive coil assembly and the ultimate temperature of the metallic tubes to control the vapor quality, vapor pressure, and vapor temperature.

The system described in FIG. 6 can continue the vapor treatment using the intrauterine pressure control system until a procedure timer reaches its prescribed time limit 618. Alternatively or in addition, the treatment can be constructed to terminate once a certain intrauterine temperature is achieved, a pre-determined flow or volume of vapor is reached, or the monitoring of the outflow temperature or constituents reach a certain level, or combinations of the above to provide either a predetermine ablation treatment or a patient tailored, prescribed ablation treatment level is achieved.

Figure 7:
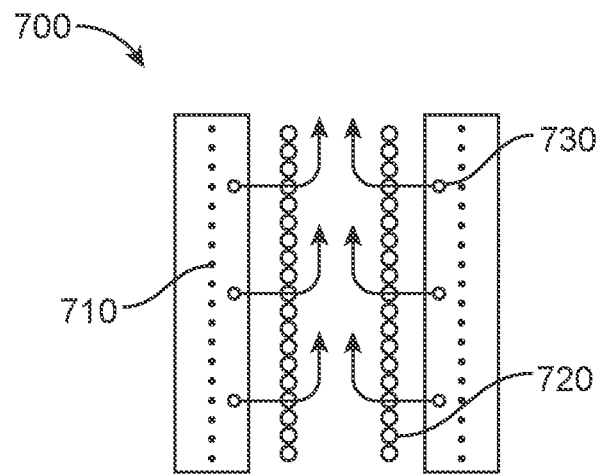
FIG. 7 illustrates a cross section of an example active air cooled induction coil system.

FIG. 7 shows a cross section of an example active air cooled induction coil system 700. In the active air cooled induction coil system 700, coils of a Litz wire 710 can be wrapped concentric to a heating coil 720. Cooling assembly 700 contains conduits for air flow seen exiting air cooling ports 730 and around Litz wire 710 within the cooling assembly. The heating coil 720 can be made from Inconel, stainless steel, or other ferromagnetic material, and can contain the fluid to be heated or vaporized. The Litz wire 710 can be connected to an RF power source and controller (not shown). Current in the Litz wire 710 can be used to heat the fluid in the heating coil 720 via inductive heating.

The cooling assembly 700 can also include air cooling ports 730. Air can be delivered to and forced through the air cooling ports 730 by conduits connected to an air source and a controller (not shown). The air from the air cooling ports 730 can be forced across the heating coil 720 and/or the Litz wire 710, dissipating heat from the cooling assembly 700.

Figure 8:
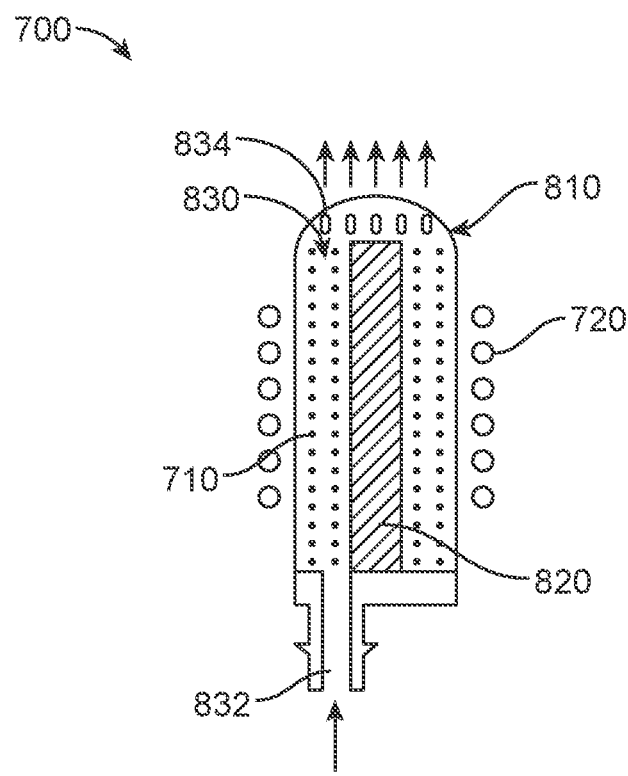
FIG. 8 illustrates a cross section of another example active air cooled induction coil system.

FIG. 8 shows a cross section of another example active air cooled induction coil system 700. As shown in FIG. 8, the coil system 700 can include a capsule 810, which can be made from a dielectric material such as ceramic, glass, mica, polysulfone, or Ultem. A heating coil 720 containing a fluid can be external to the capsule 810. A Litz wire 710 can be coiled within the capsule 810, concentric to a ferrite core 820 and within an air chamber 830. Circulating air can enter the air chamber 830 via an air input port 1634, which can be connected to a conduit and an air source driven by a controller (not shown). The circulating air can be forced through the air chamber 830 to outflow exits 834 to actively cool the Litz wire 710.

The Litz coil 710 can be cooled with two fluids. For example, the Litz coil 710 can be cooled by air flowing through the air chamber 830 and by saline or water flowing through the heating coil 720. The fluid entering the heating coil 720 and/or the air entering the air input port 1634 can be at about room temperature (e.g., about 70 to 75° F.), or about 100° F., for example due to pre-heating of the air and or water by thermal conduction via the outbound water and/or air.

The Litz coil 710 can use 500 W initially for about 30 seconds (e.g., 10 to 50 seconds, more narrowly 20 to 40 seconds) and then 350 W electrical power for about 110 seconds into the Litz coils during use. The total treatment time can be about 110 seconds to about 170 seconds, for example 140 seconds total. During a single treatment or use, the Litz coil can use about 21 to about 27 kJ, for example about 24 kJ, for example over about 140 seconds.

Figure 9A:
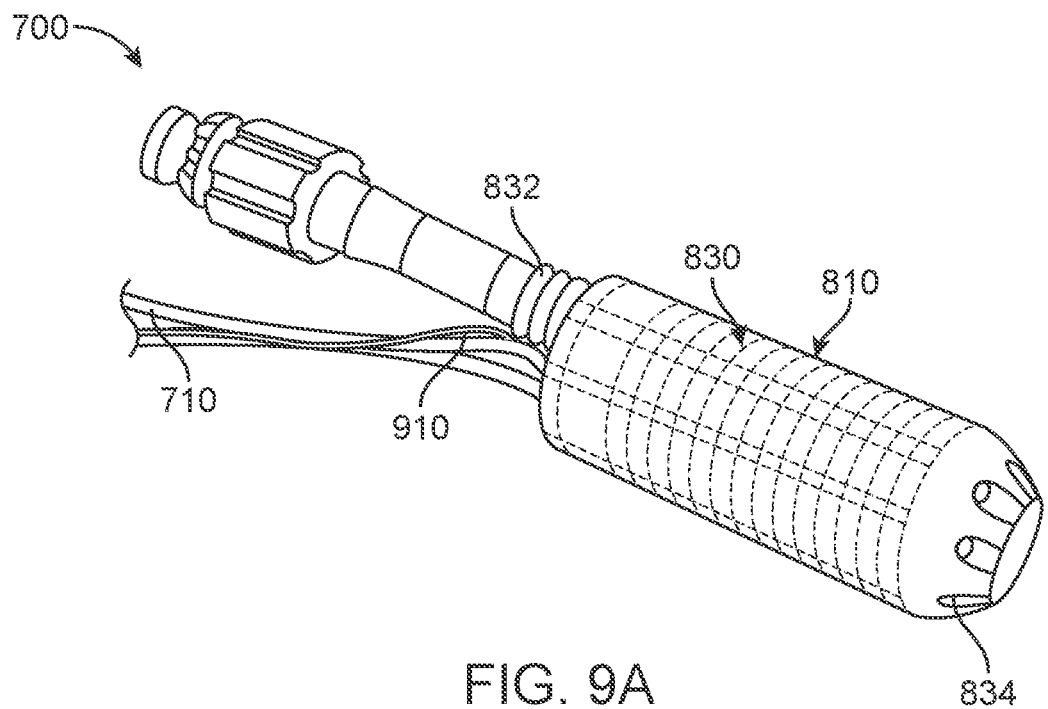
FIGS. 9A-9D illustrate an example active air cooled induction coil system.

FIGS. 9A-9D show photographs of the example active air cooled induction coil system 700. In FIG. 9A, the capsule 810 is seen with Litz wire 710 that can be connected to an RF power source and a controller (not shown). Alongside Litz wire 710 in FIG. 9A is a wire thermocouple 910, which can provide temperature monitoring of the induction coil system 700. Within the capsule 810, the Litz wire 710 can be wound around the ferrite core 820 (not visible) to form a coil. Circulating air from an air source and controller can be connected to the air input port 1634. Air can enter the capsule 810 via the air input port 1634 and exit the capsule 810 at air outflow exits 834, cooling the Litz wire 710 within air chamber 830 as the air is forced through the capsule 810.

Figure 9B:
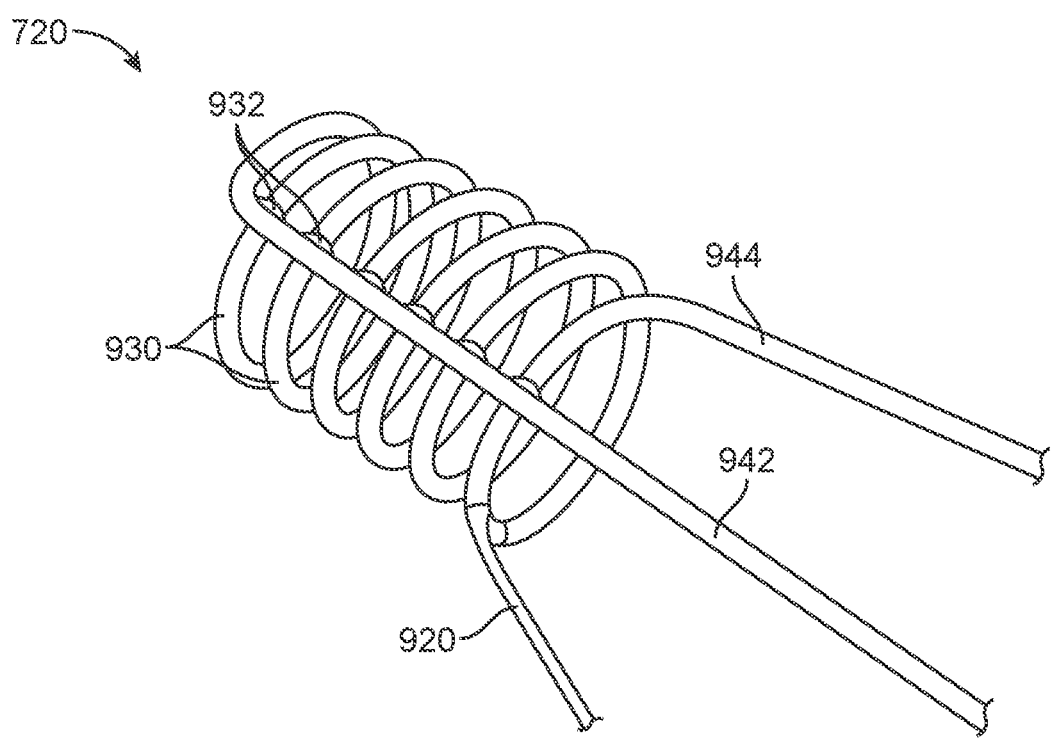

FIG. 9B shows a photograph of an example heating coil 720 with a thermocouple wire 920 and heating coil wraps 930. Fluid can enter the heating coil 720 via a fluid input 942 and wind through multiple wraps 930, which can be held in place by solder or weld joints 932. The fluid can be heated or vaporized as it passes through the wraps 930, and the heated or vaporized fluid can be delivered to a vapor delivery device via a fluid output 944.

Each wrap 930 and solder joint 932 shown in FIG. 9B can create an electrical single turn. Six full (360°) turns are illustrated in FIG. 9B within the single fluidic pathway with fluid input tube 942 and vapor output tube 944, but the heating coil 720 may have more or less than six full turns.

With the desire to keep the induction coil system 700 small while also efficient to reduce heating the Litz wire 710 and ferrite core 820, design considerations for elements of the induction coil system 700 may include magnetizing and leakage inductance, load resistance, turns ratio between the Litz wire 710 and heating coil 720, diameter of the Litz wire 710, and the volume and shape of the ferrite core 820. The number of turns, length of turns, cross-sectional area and resistivity of the material in the heating coil 720 may affect a load resistance, which can be matched, via a turns ratio to the Litz wire 710, to a load resistance that is practical to drive using the RF power supply and cable.

Figure 9C:
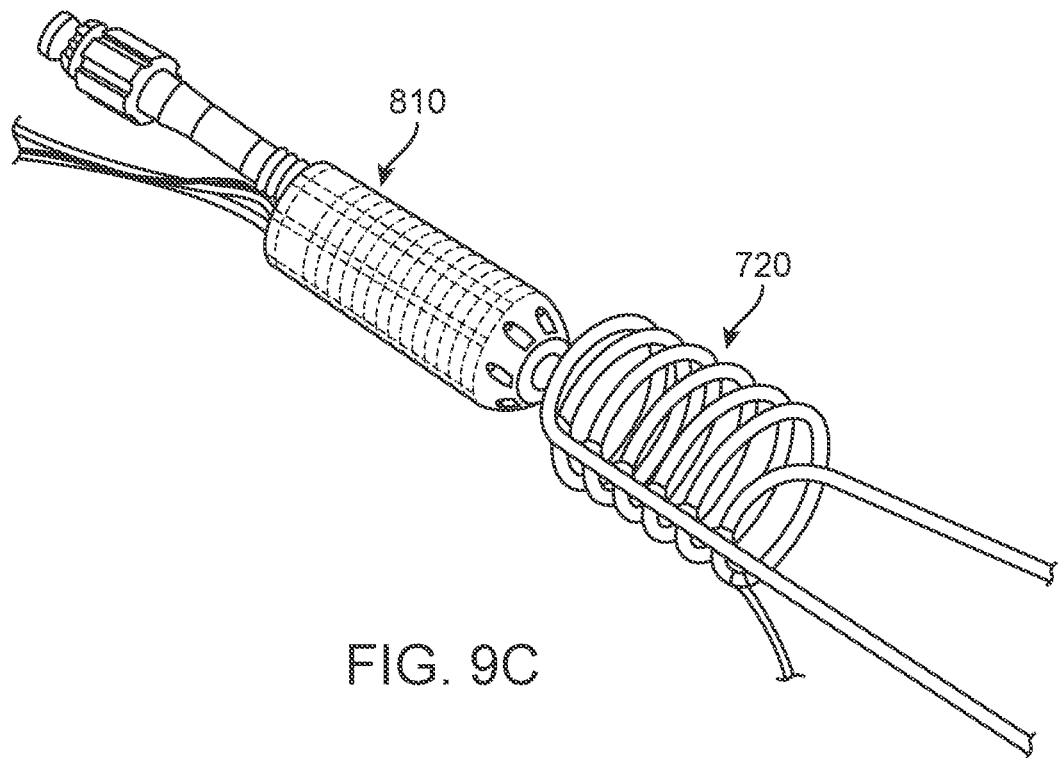
Figure 9D:
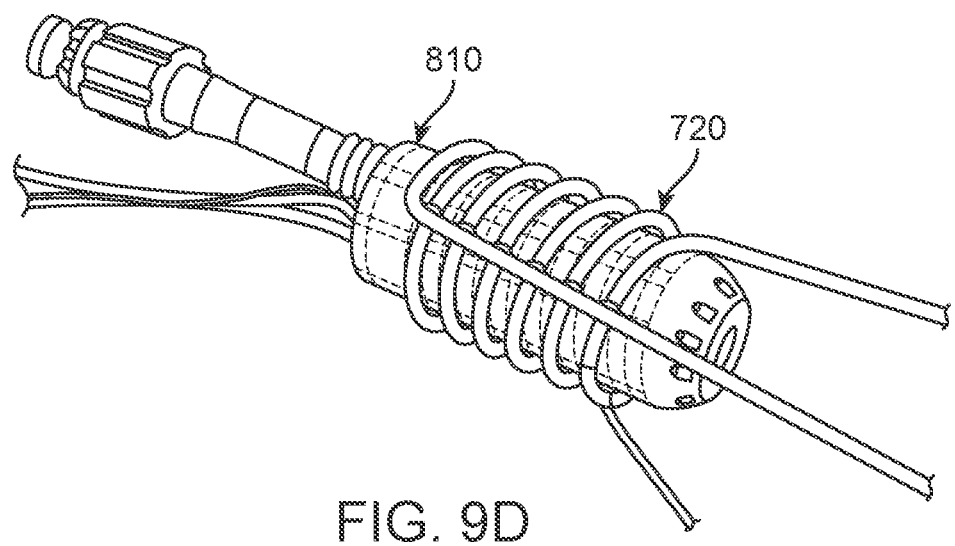

FIG. 9C shows an example of the capsule 810 and heating coil 720 prior to final assembly, while FIG. 9D shows the capsule 810 insert concentrically within the heating coil 720 to complete the active air cooled induction coil system 700. Final assembly can be performed in the manufacturing process or as the components are assembled by the end user. As an example, capsule 810 can be configured as a reusable component that is inserted into a disposable vapor delivery device including the heating coil 720. The capsule 810 can be reused for multiple procedures, while the heating coil 720 and other components of the disposable vapor delivery device can be disposed after each procedure.

FIGS. 10A-10G illustrate different views of a variation of the capsule 810.

Figure 10A:
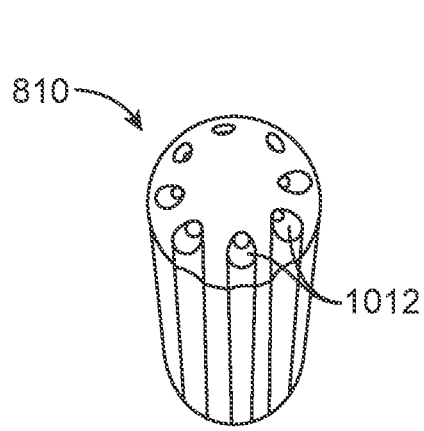
FIGS. 10A-10E illustrate a capsule in an active air cooled induction coil system.
Figure 10B:
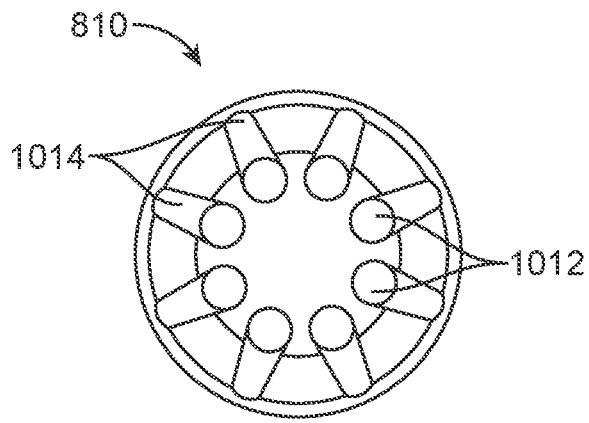
Figure 10C:
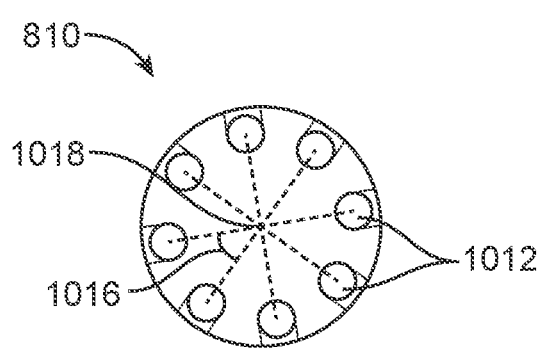

FIGS. 10A-10G illustrate that the capsule 810 can include multiple ports 1012 facilitating air flow into the capsule 810 or air flow out of the capsule 810. As shown in FIG. 10B, the ports 1012 can be at equal radii as each other (i.e., the other ports 1012 can be at the same radii as each other). As shown in FIG. 10C, the ports 1012 can be at evenly distributed angles 1016 as each other from a longitudinal axis 1018 of the capsule 810 (e.g., eight ports spread angularly at 0, 45, 90, 135, 180, 225, 270, 315, and 360 degrees, respectively, about the longitudinal axis 1018).

The ports 1012 can be at unequal radii to each other, and can be at unevenly distributed angles from the longitudinal axis 1018 of the capsule as each other.

Figure 10D:
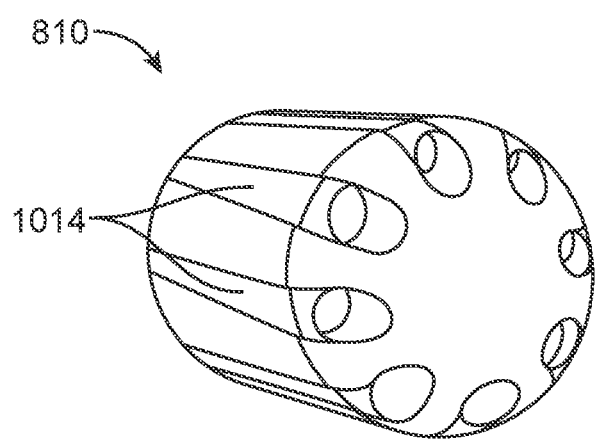
Figure 10E:
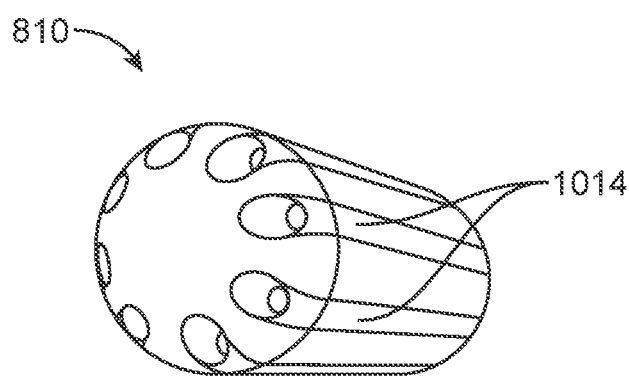

FIGS. 10B, 10D, and 10E illustrate bores or grooves 1014 on an inner surface of the capsule 810. The bores or grooves can be material absent during molding of the capsule and/or can be material removed from the capsule by milling or drilling. The bores 1014 can extend from a proximal terminal end of the capsule to a distal terminal end of the capsule. The bores can longitudinally extend at least the corresponding length of the Litz coil. The bores 1014 and the ports 1012 can together form a plurality of airflow channels through the capsule 810.

Figure 11:
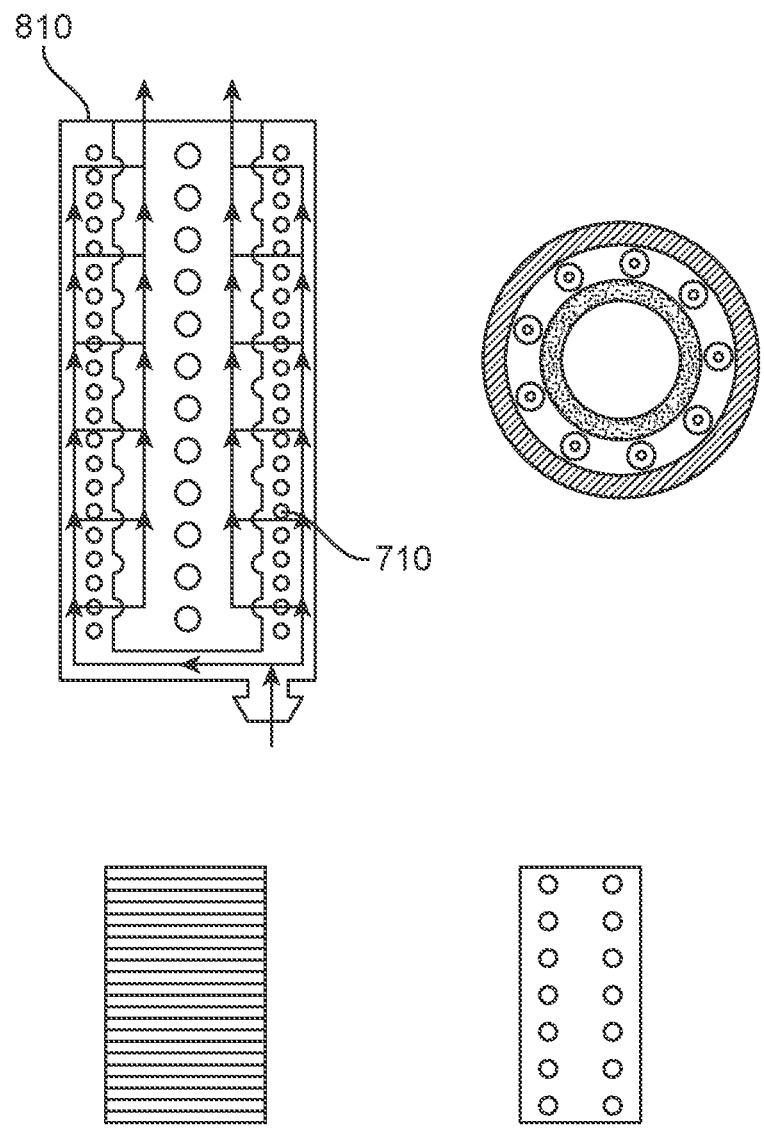
FIG. 11 illustrates that cooling air can flow transversely or laterally within the capsule.

FIG. 11 illustrates that cooling air can flow transversely or laterally within the capsule. Cooling air can flow along the length of the Litz coil 710, and/or between the windings of the Litz coil 710, either between windings that are spaced before air is blown between them and/or windings in contact with each other before air blows between them.

Closed-Loop Ferrite Core Inductive Coil Assembly

Figure 12A:
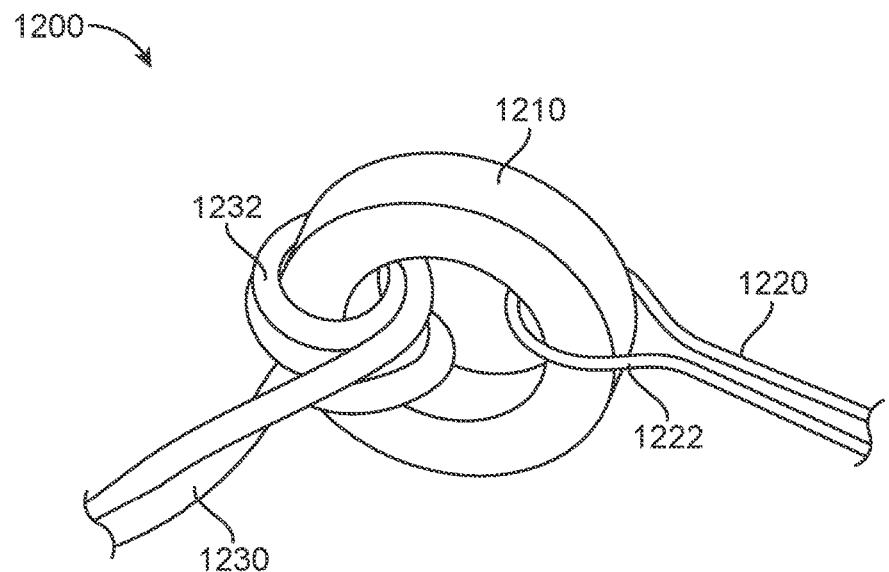
FIGS. 12A and 12B illustrate example inductive coil assemblies including closed-loop ferrite cores.

FIG. 12A illustrates an alternate ferrite core, inductive coil assembly 1200. In the inductive coil assembly 1200, a ferrite core 1210 can be configured in a closed loop, circular configuration. The closed loop can be circular, elliptical, square, rectangular, or other multi-sided geometric configuration. Fluid can flow into the inductive coil assembly 1200 via a metallic tube 1220. Metallic tube 1220 is shown in FIG. 12A with one wrap 1222 around ferrite core 1210, but may instead have multiple wraps around, within, along-side, or tangential to the ferrite core, or combinations thereof. An insulated wire 1230 is shown in FIG. 12A with multiple wraps 1232 around the ferrite core 1210. The insulated wire 1230 can be Litz, magnetic, or other wire source that is supplied with electrical current from the RF power source (not shown). Wraps 1232 can be configured around, within, or tangential to the ferrite core 1210. Wraps 1232 can be configured as a singular wrap or multiple wraps. The closed loop ferrite core 1210, by its configuration, can reduce stray currents and heat accumulation in the insulated wire 1230.

Figure 12B:
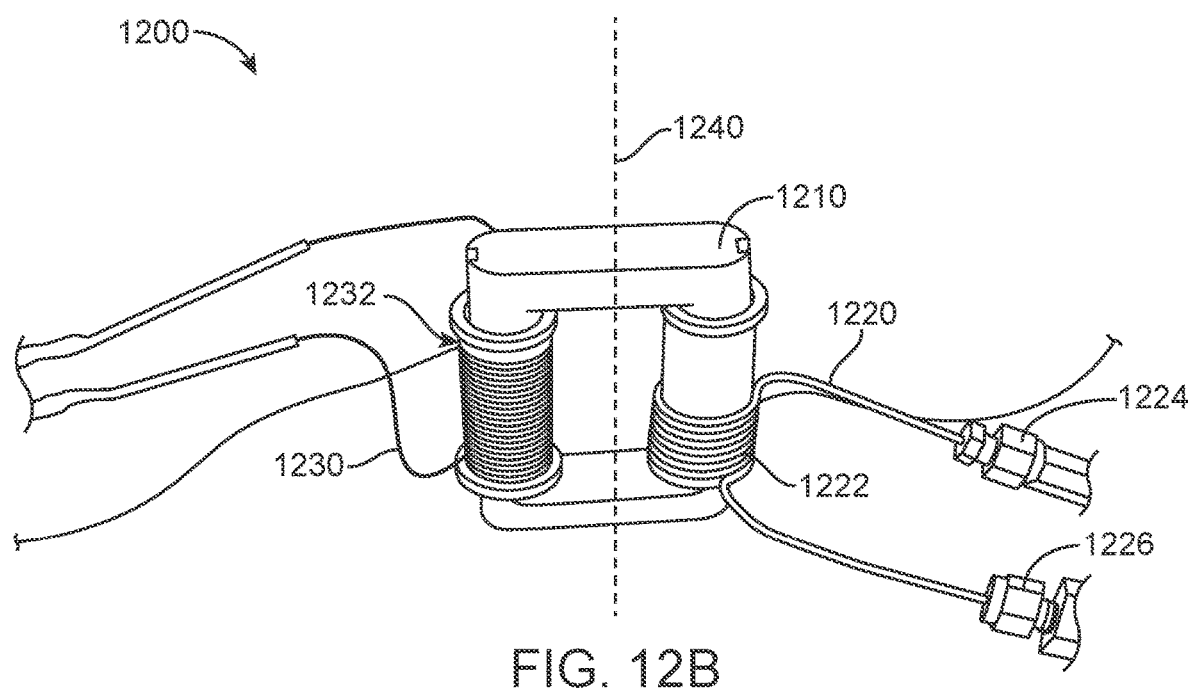

FIG. 12B illustrates that the inductive coil assembly 1200 can have a closed loop, ferrite core 1210, or combinations thereof. The ferrite core 1210 can be substantially rectangular in shape, substantially round, or have another multi-sided geometry. A metallic tube 1220 configured to carry fluid can be wrapped one or more times around a side of the ferrite core 1210. The metallic tube 1220 can have an input port 1224 at one end that supplies fluid to the inductive coil assembly 1200 and an output port 1226 that delivers the heated fluid or vapor to the delivery device (not shown) at the other end. The metallic tube 1220 can include one or more wraps 1222 around the ferrite core 1210. Although the wraps 1222 are shown on one side of the ferrite core 1210 in FIG. 12B, the wraps 1222 can be configured on multiple sides and throughout the ferrite core 1210, or can be configured tangentially to or alongside the ferrite core 1210.

The inductive coil assembly 1200 can also include a Litz wire 615 configured to carry electrical current from an RF power source (not shown). Litz wire 615 can have one or more wire wraps 1232 around a side of the ferrite core 1210. Wire wraps 1232 can be configured on multiple sides and throughout the ferrite core 1210. Current in the wire wraps 1232 can generate a magnetizing inductance to heat and/or vaporize fluid in the metallic tube 1220.

The ferrite core 1210 can be provided in multiple pieces that are placed together by the end user or in manufacturing. In FIG. 12B, dotted line 1240 represents a potential splitting point for the closed loop, ferrite core 1210. Components to the left of the dotted line 1240 can be reusable components, while those on the right side of the dotted line 1240 can be disposable. For example, the components to the left of the dotted line 1240 can be placed in a cartridge configured to fit into a disposable vapor delivery device. During use, a physician can insert the cartridge into the vapor delivery device to couple with the components to the right side of the dotted line 1240. The coupling engagement can be facilitated by the left and right sides of the ferrite core 1210 being pressed together by cams, friction fit, tongue and groove engagement, or other mechanical detents that allow the two sides of the ferrite core 1210 to couple sufficiently to complete the inductive coil assembly 1200, as shown in FIG. 12B, within the vapor delivery device.

The ferrite core 1210 can be separable in manners other than that shown in FIG. 12B to facilitate manufacturing or the vapor delivery device configuration. FIG. 12B illustrates splitting the ferrite core 1210 into two pieces, but the ferrite core 1210 can come in multiple pieces (i.e. greater than 2) depending upon the assembly technique and configuration of the desired magnetic field. As an example, the ferrite core 1210 can have coupleable top and bottom halves each including ferrite side panels, ferrite front and back panels, central ferrite cores, or additional ferrite cores for mounting the metallic heating tube 1220 and insulated or Litz wire 615.

Figure 13A:
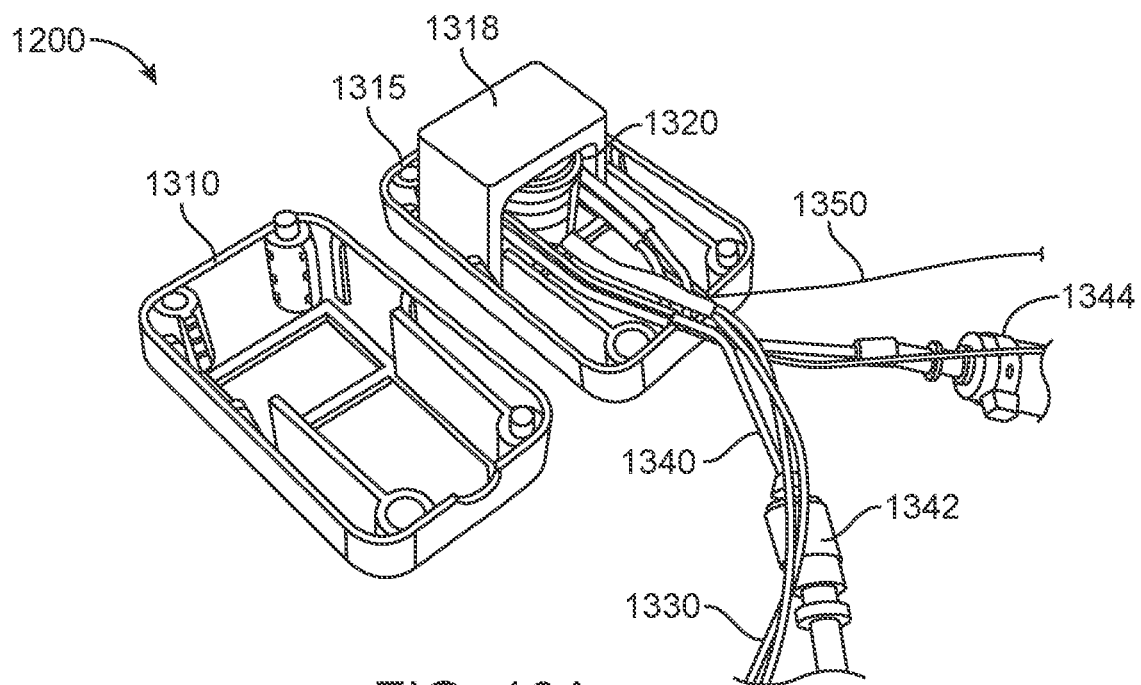
FIGS. 13A-13B illustrate an example inductive coil module assembly with separable bottom and top container halves.

FIG. 13A shows an example inductive coil module assembly 1200 with separable bottom and top container halves 1310 and 1315. When coupled, the bottom and top container halves 1310 and 1315 can encase the entire inductive coil assembly 700. Inductive coil support frame 1318 can reside within container halves 1310 and 1315 and hold separable pieces of a closed loop ferrite core 1320 together. The inductive coil support frame 1318 can be made from heat shrink tubing that holds the pieces of the ferrite core 1320 together for electrical coupling.

The inductive coil module assembly 1200 can include an insulated wire 1330 configured to carry an electric current, a metallic tube 1340 configured to carry a fluid, and a thermocouple wire 1350. The insulated wire 1330 and metallic tube 1340 can each be coiled around a portion of the ferrite core 1320. Electric current in the insulated wire 1330 can generate a magnetizing inductance to heat the metallic tube 1340. The metallic tube 1340 can include an input 1342 providing fluid into the inductive coil module assembly 1200 and an output 1344 delivering vapor and/or heated fluid to a patient. The thermocouple wire 1350 can be used to measure temperature within the inductive coil module assembly 1200 during treatment.

The inductive coil support frame 1318 and container halves 1310 and 1315 can include openings to allow a thermocouple wire 1350, insulated wires 1330, input metallic tube 1342, and metallic vapor output tube 1344 to exit the inductive coil module assembly 1200.

Figure 13B:
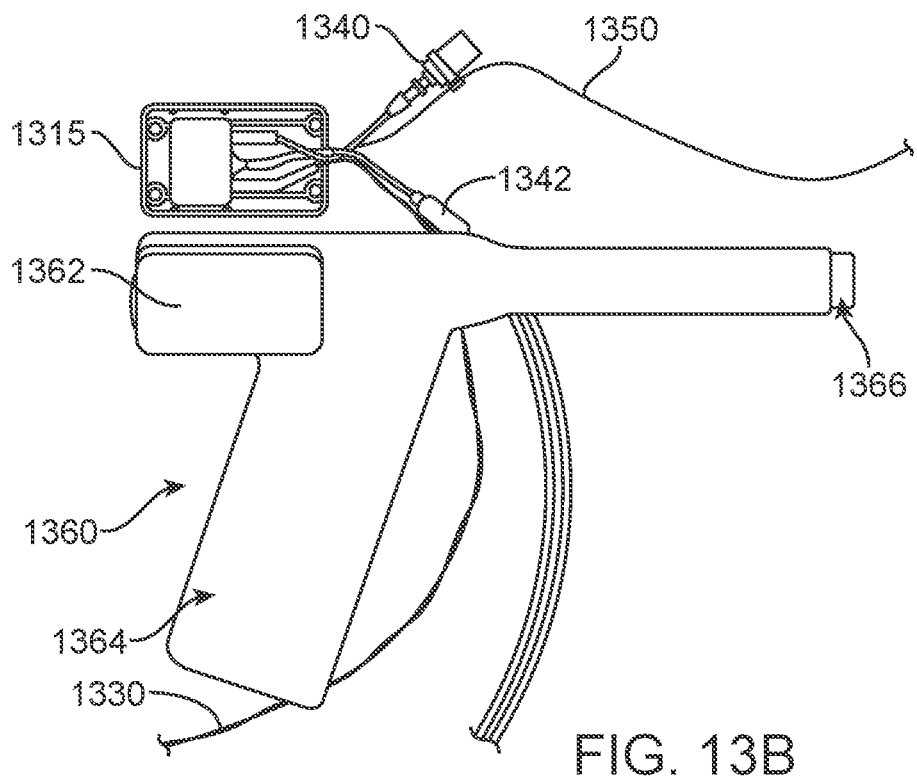

FIG. 13B shows the inductive coil module assembly 1200 within bottom container half 1315 alongside a vapor delivery device 1360. The vapor delivery device 1360 can include the top container half 1310, and the bottom container half 1315 can be configured to fit into the vapor delivery device 1360 to couple with the top container half 1310. When placed within the vapor delivery device 1360, the inductive coil module assembly 1200 can reside at location 1362 above a handle 1364, which can be used by a user to hold the device 1360. The vapor delivery device 1360 can have a distal end 1366 where vapor generated in the inductive coil module assembly 1200 exits the device and enters a patient.

Figure 14A:
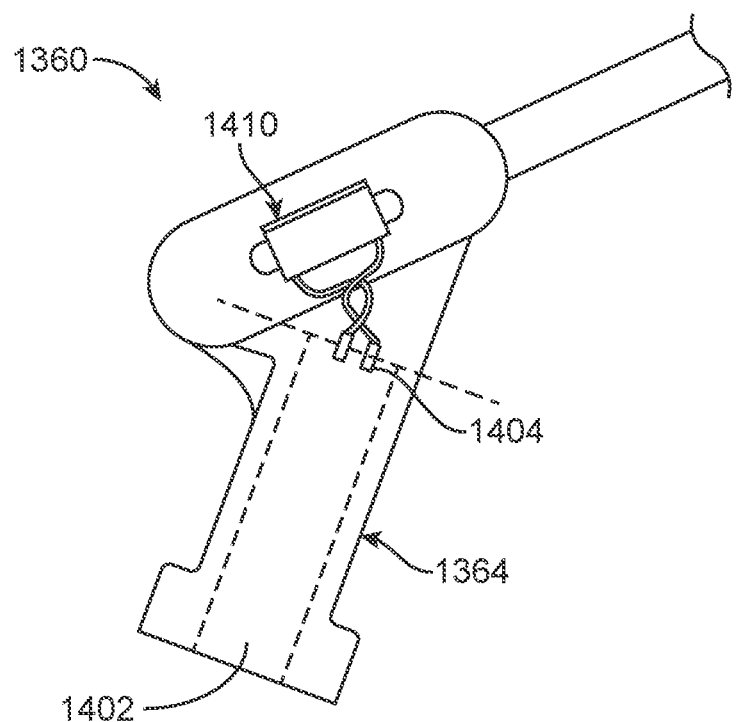
FIGS. 14A-14B are cut away views of an example vapor delivery device.

FIG. 14A illustrates a cut away side view of an example vapor delivery device 1360 with handle 1364. Within the handle 1364 is handle hole 1402 that can accept a cartridge and connections to controller (not shown). A closed loop ferrite core induction coil system 1410 can be contained with the vapor delivery device 1360, and can be coupleable to an RF power source via electrical connectors 1404.

Figure 14B:
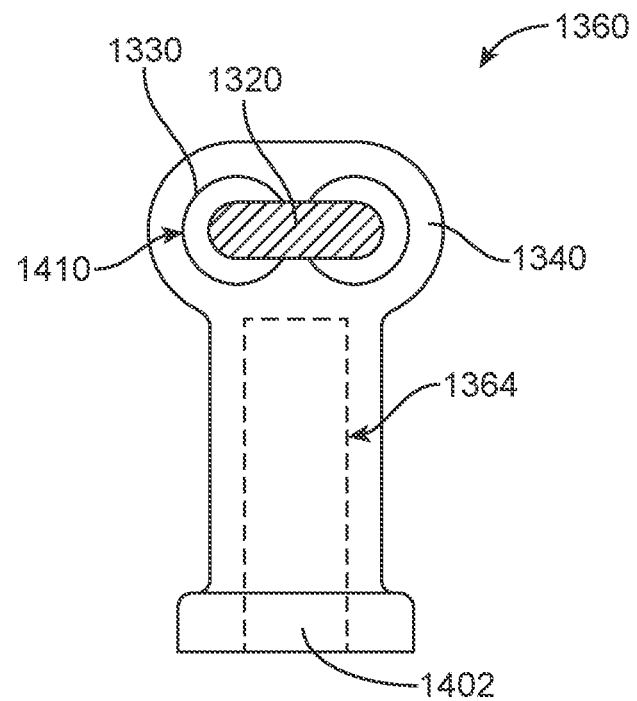

FIG. 14B illustrates an example cut away axial view of the vapor delivery device 1200 with induction coil system 1410. The induction coil system 1410 can include closed loop ferrite core 1320 with heating coil 1340 wrapped around a first part of the core 1320 and Litz wire 1330 wrapped around a second part of the core 1320. Current in the Litz wire 1330 can generate a magnetizing inductance to inductively heat the heating coil 1340.

Figure 15:
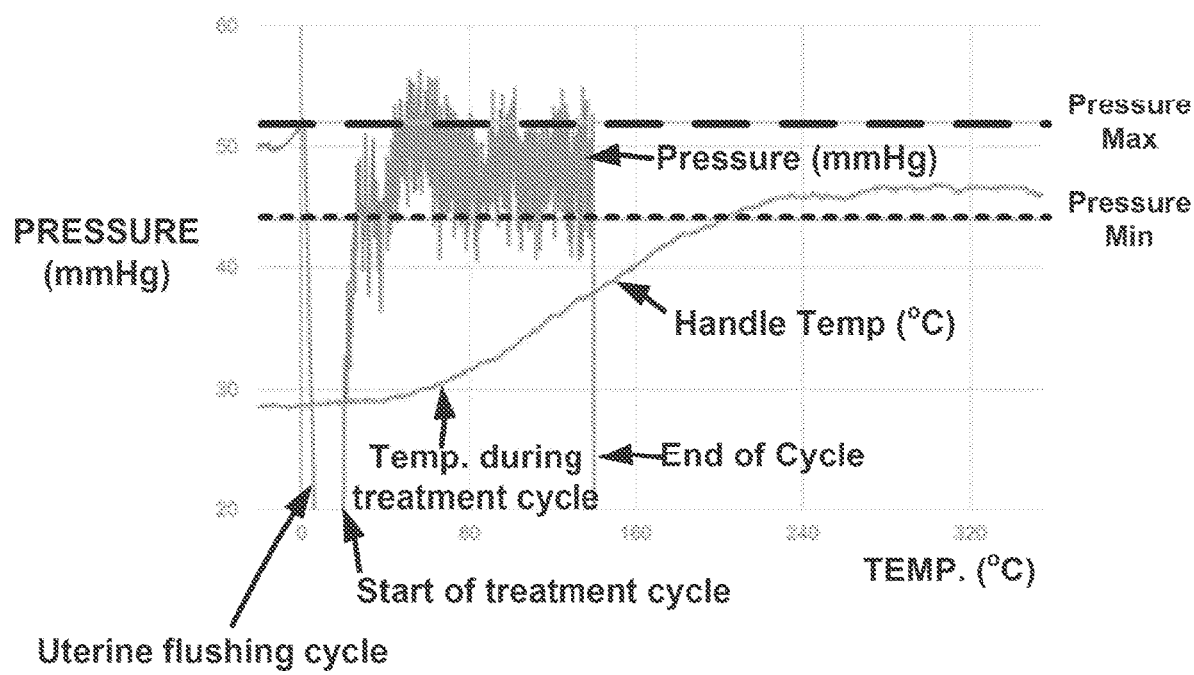
FIG. 15 is a graph illustrating temperature and pressure in an induction coil assembly during a treatment cycle.

Graph 2 in FIG. 15 illustrates that the induction coil assembly 1200 with a closed loop ferrite core can reduce thermal buildup. In the experiment represented in Graph 2, the induction coil assembly produced vapor for a time duration of 140 seconds (as shown on the X axis), for example to perform uterine endometrial ablation. The Handle Temp line shows a temperature of the handle 1364 measured by a thermocouple during the ablation treatment cycle. In the example of Graph 2, the temperature gradually rises to 38° C. during the treatment cycle to the 140 second mark at the end of the treatment cycle. The handle temperature continues to rise in this experiment when the fluid delivery is terminated in the handle and plateaus slightly above 45° C. The handle temperature may be regulated to stay below 48° C., the temperature set by the IEC 60601 standard for a two minute exposure duration to skin or tissue for thermal necrosis.

The Pressure line in Graph 2 illustrates example pressure regulation during the treatment cycle within a Pressure Max and Pressure Min range. This pressure range can be defined for the procedure performed using the vapor delivery device. For example, pressure for a uterine endometrial ablation procedure may have a pressure max of 70 mmHg to reduce the possibility of vapor entering or traversing the fallopian tubes. The pressure min for the endometrial ablation procedure may be 20 mmHg to provide enough distension pressure to expose the interior of the uterine cavity to vapor. The pressure may be regulated to approximately 48 mmHg, for example. The fluctuations of pressure shown in Graph 2 reflect the dynamic environment of the uterine cavity, the condensation of vapor as it contacts the interior wall, and the continuous flow configuration of the vapor delivery device with return lumen and outflow conduit. Graph 2 illustrates that the pressure regulation system of the vapor delivery device can rapidly respond to the constantly changing intrauterine pressure environment and can regulate the pressure within a specified pressure range.

FIGS. 16A-16H illustrate example components of the inductive coil module assembly 1200 as they are assembled.

Figure 16A:
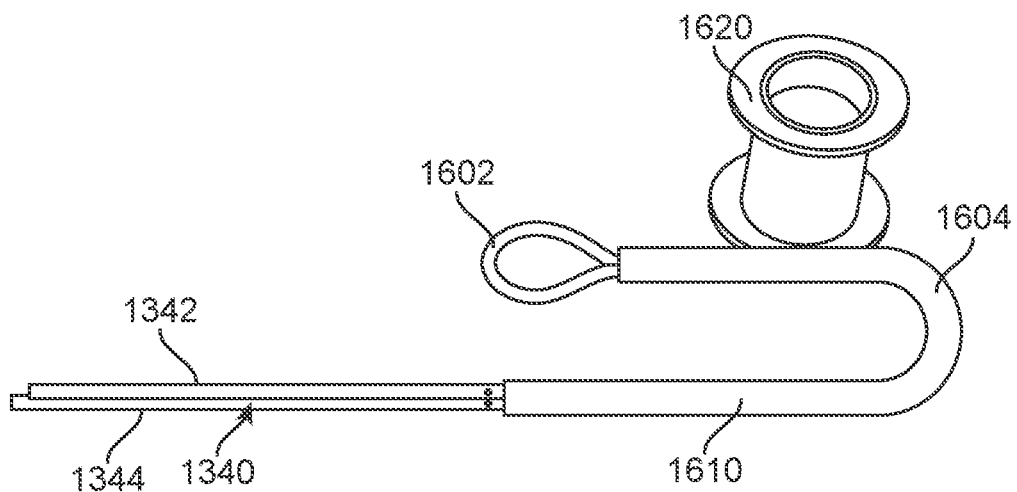
FIGS. 16A-16H illustrate example components of an inductive coil module assembly as they are assembled.

FIG. 16A shows the metallic tube 1340 with input 1342 and output 1344. The metal tube 1340 can be constructed from stainless steel, Inconel, or other metal as described earlier. Metallic tube 1340 can be configured with a loop 1602 and the input 1342 and output 1344 adjacent to or in contact with one another. An insulating tube cover 1610, constructed from Teflon, silicone, rubber, or other thermal insulator, can enclose at least part of the metal tube 1340.

The metal tube 1340 can be wrapped or bent, for example at bend 1604, around a bobbin 1620. As shown in FIG. 16A, the bobbin 1620 can be configured as a dowel, bobbin, or tube. The bobbin 1620 can comprise a material with a low electrical conductivity. The bobbin 1620 can also have a low thermal conductivity. For example, the bobbin 1620 can be made from glass, ceramic, mica, or plastics such as polysulfone or Ultem. The bobbin 1620 can aid manufacturing of the inductive coil assembly 1200.

Figure 16B:
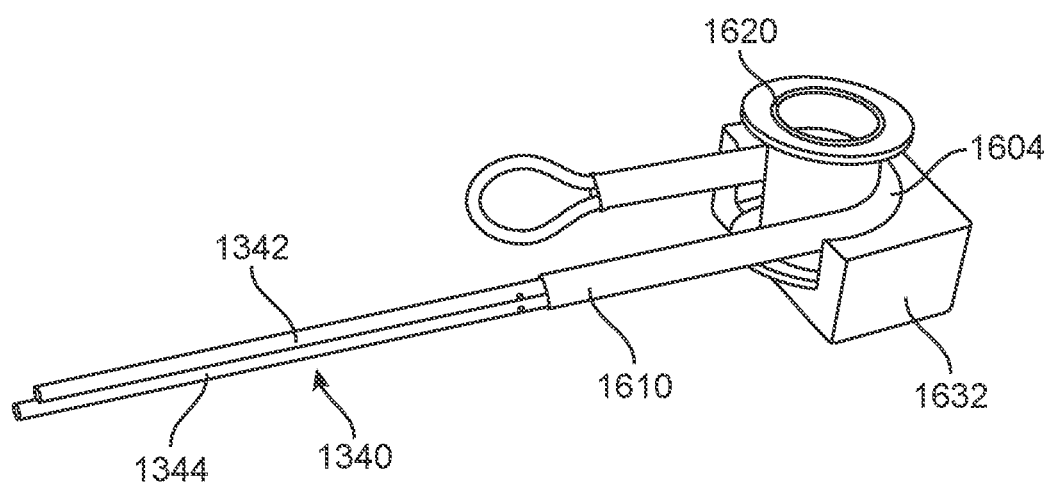

FIG. 16B shows the metallic tube 1340 with bend 1604 wrapped around the bobbin 1620, which together can fit within a bottom half 1632 of the closed loop ferrite core 1320.

Figure 16C:
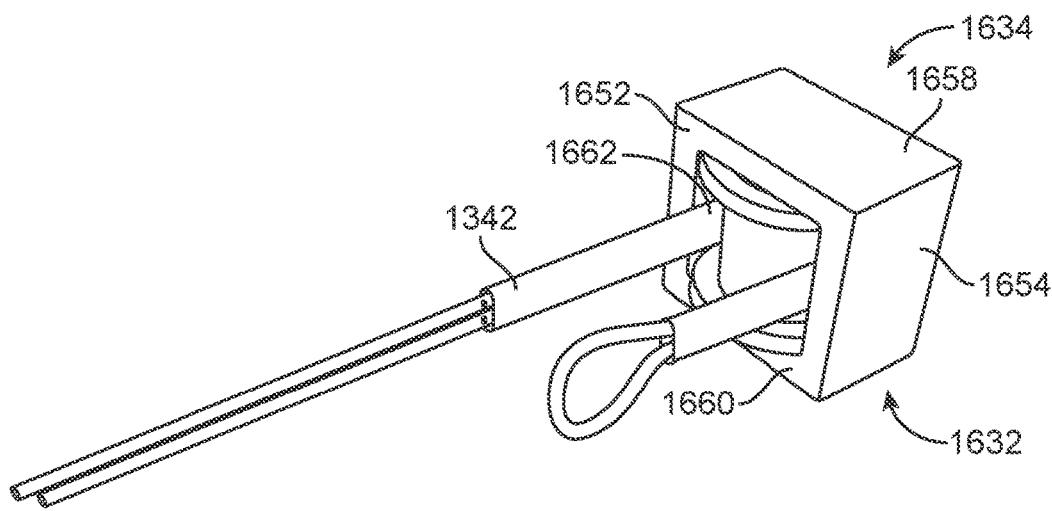

FIG. 16C shows a ferrite closed loop top half 1634, which can be placed above the matching ferrite closed loop bottom half 1632 to complete the closed loop.

Figure 16D:
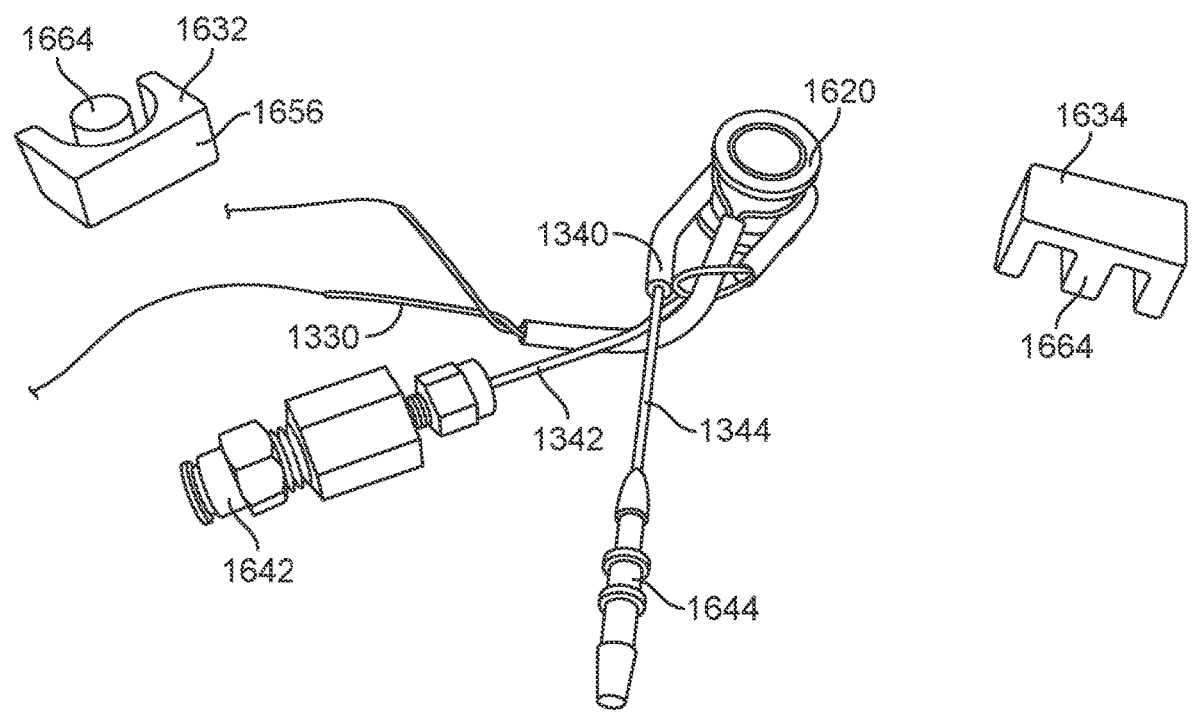

FIG. 16D shows the insulated wire 1330 can also be coiled around the bobbin 1620. The insulated wire 1330 can be coiled multiple times around the bobbin 1620 and the metallic tube 1340 can be bent or coiled around the bobbin 1620 outside and concentric to the insulated wire 1330. The metallic tube 1340 can alternatively be placed between the bobbin 1620 and the insulated wire 1330. FIG. 16D also shows that an input port 1642 can be coupled to the input 1342 of the metallic tube 1340 and an output port 1644 can be coupled to the output tube 1344.

FIGS. 16C-16D further illustrate that a closed loop ferrite core in the shape of a box can be formed by the top half 1634 and the bottom half 1632. The box can include one or more of a left side 1652, a right side 1654, a back side 1656, a top side 1658, and a bottom side 1660 composed of ferrite and formed integrally or connected in an abutting configuration. Figure BB3C shows that the top half 1634 and bottom half 1632 when coupled can form a shape approximating a rectangular prism, where each of the left and right sides 1652 and 1654, back side, top side 1658, and bottom side 1660 are substantially rectangular in shape. The box can alternatively approximate a cylinder, where the top side 1658 and bottom side 1660 are substantially circular in shape and one or more rectangular sides couple the top and bottom. The ferrite core can approximate other shapes, such as a sphere, a toroid, or an ellipsoid. The box formed by coupling the top half 1634 to the bottom half 1632 may be integrally formed, separable, or releasably coupleable. Furthermore, the box can be constructed from more than two ferrite pieces.

When coupled, the top half 1634 and bottom half 1632 can provide an opening 1662 allowing the insulated wire 1330 and metallic tube 1340 to enter and exit the box. The top half 1634 and bottom half 1632 can provide more than one opening. For example, the metallic tube 1340 and insulated wire 1330 can enter the box through a first opening and exit the box through a second opening, or the metallic tube 1340 can enter and exit the box through the first opening and the insulated wire 1330 can enter and exit the box through the second opening. As another example, the box can include a first opening through which the metallic tube 1340 enters the box, a second opening through which the metallic tube 1340 exits the box, a third opening through which the insulated wire 1330 enters the box, and a fourth opening through which the insulated wire 1330 exits the box.

Each of the top half 1634 and bottom half 1632 can include a ferrite center 1664. The ferrite center 1664 can be formed integrally with the sides, top, and/or bottom of the box, or can directly contact or abut one or more of the sides, top, or bottom. The central pin may be positioned at approximately a center of the ferrite core when the top half 1634 is coupled to the bottom half 1632.

Figure 16E:
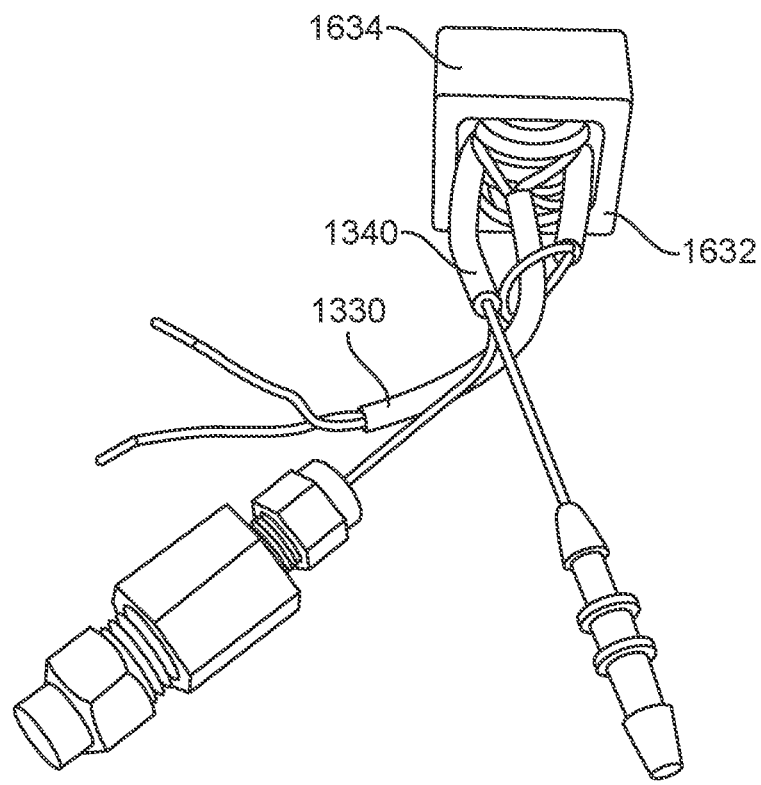

FIG. 16E illustrates that the bobbin 1620, with metallic tube 1340 and insulated wire 1330, can be enclosed within the closed loop ferrite core formed by coupling the ferrite closed loop bottom half 1634 to the ferrite closed loop top half 1634.

Figure 16F:
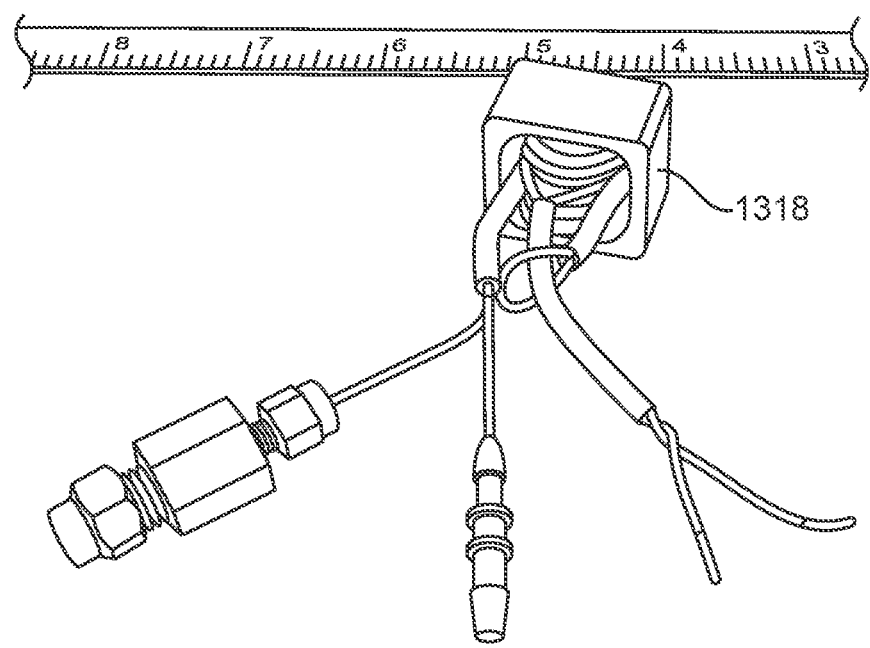
Figure 16G:
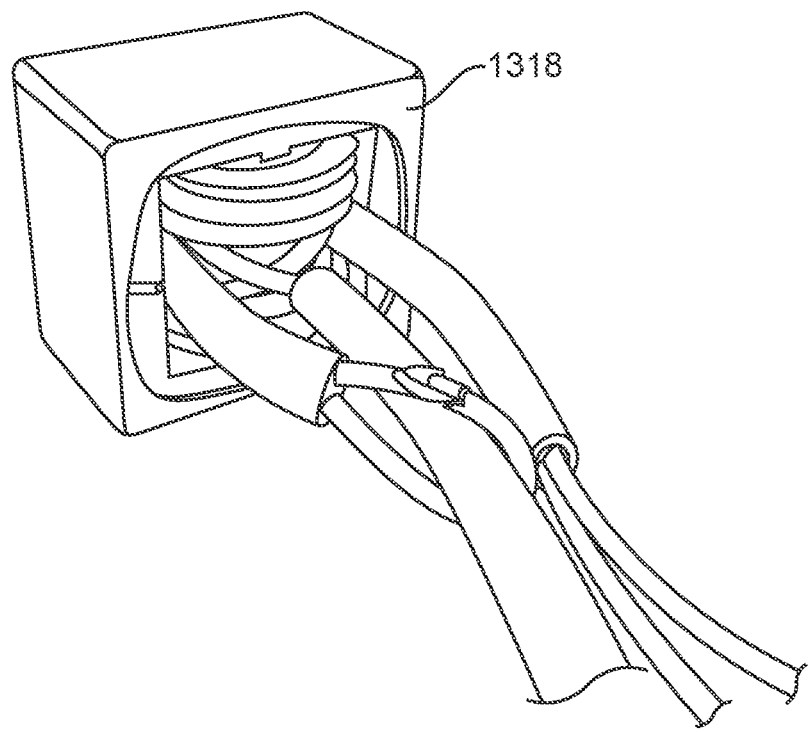

FIGS. 16F-16G show the inductive coil support frame 1318 can be assembled by wrapping the ferrite closed loop bottom half 1632 and top half 1634 in a heat shrink tubing. The ferrite core halves 1632 and 1634 can be mechanically pressed together by the heat shrink 1318. The completion of the magnetic field of multiple pieces of a ferrite core can be accomplished with mechanical cams that physically press the ferrite core pieces together without the use of heat shrink 1318.

Figure 16H:
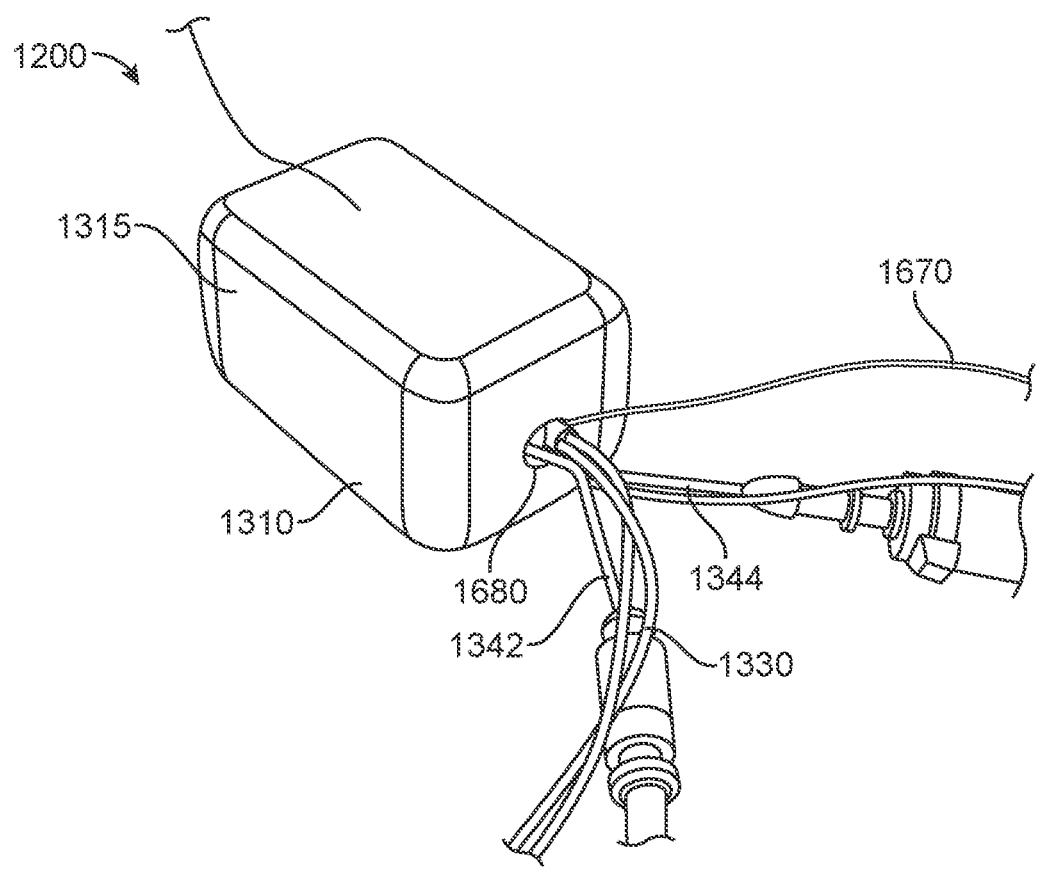

FIG. 16H shows an example of the inductive coil module assembly 1200 enclosed within the combined bottom and top container halves 1310 and 1315, with thermocouple wire 1670, metallic tube input 1342, metallic tube output 1344, and insulating wire 1330 exiting through a hole 1680.

Figure 17A:
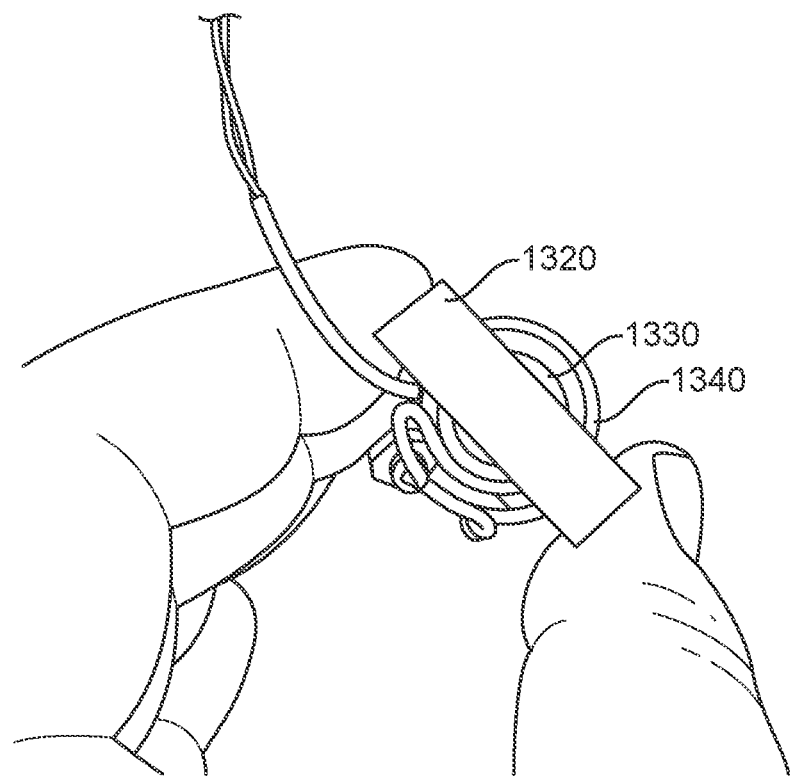
FIGS. 17A-17B illustrate an example closed-loop ferrite core.
Figure 17B:
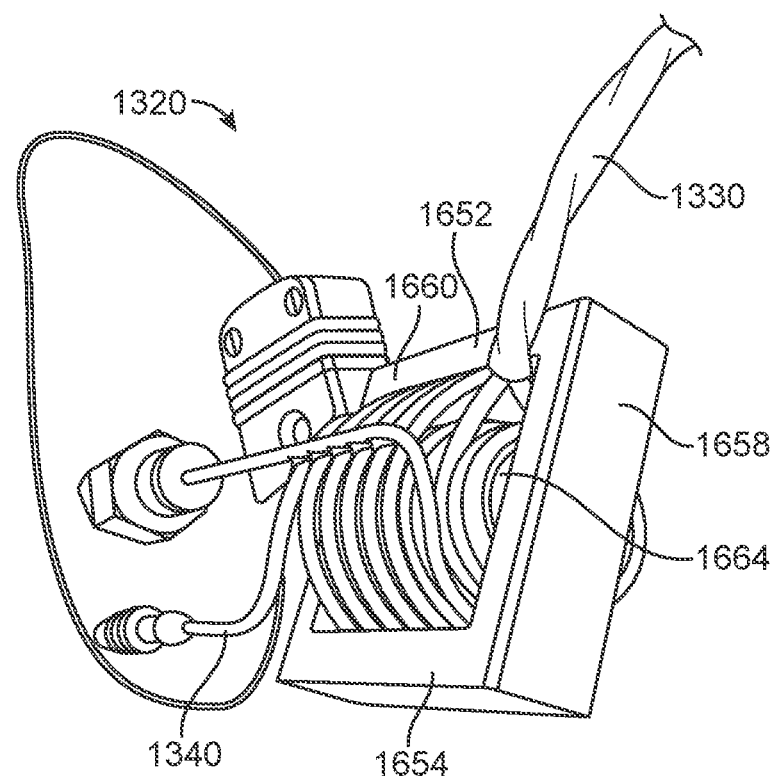

FIGS. 17A-17B illustrate another example closed-loop ferrite core 1320. The ferrite core 1320 can have a substantially open shape surrounding a portion of the metallic tube 1330 and insulated wire 1340. As shown in FIG. 17B, the core can include a left side 1652, a right side 1654, a top side 1658, and a bottom side 1660, with open back and front sides. The left side 1652, right side 1654, top side 1658, and bottom side 1660 may each be substantially rectangular in shape, or may be formed to approximate other shapes. For example, the ferrite core 1320 may comprise a toroidal or circular shape. The metallic tube 1330 and insulated wire 1340 can be coiled around a ferrite center 1664 coupling the top side 1658 to the bottom side 1660.

Figure 18:
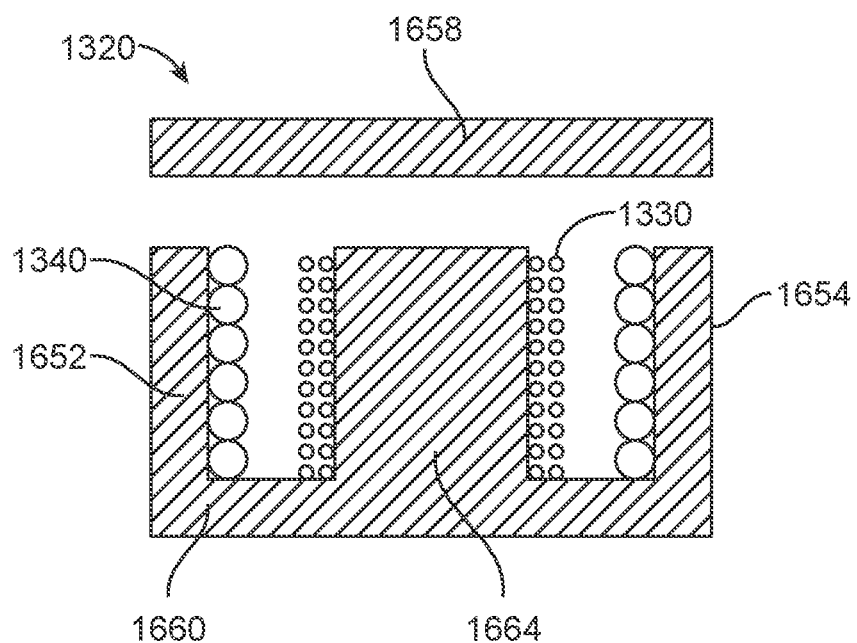
FIG. 18 illustrates an example side cross section of an inductive coil module assembly.
Figure 19:
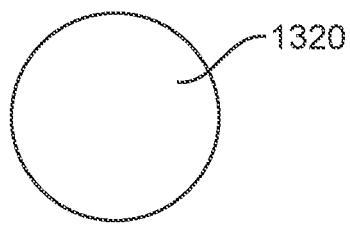
FIG. 19 illustrates an example top view of an inductive coil module assembly.
Figure 20:
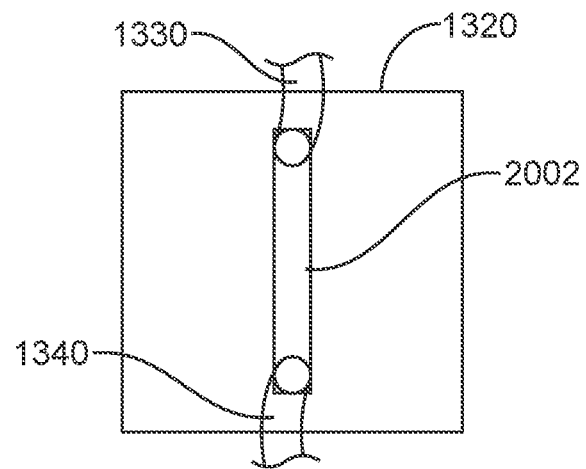
FIG. 20 illustrates an example front view of an inductive coil module assembly.

One or more wraps of each of the metallic tube 1340 and insulated wire 1330 can be enclosed within or surrounded by the ferrite core 1320. Each of the one or more wraps can wrap concentrically to the ferrite center 1664. Each wrap may be an arc of less than 360 degrees (e.g., 180 degree), or may be a closed 360-degree arc. FIG. 18 illustrates an example side cross section of the metallic tube 1340 and insulated wire 1330 wrapped a plurality of times and concentrically around the ferrite center 1664, with the insulated wire 1330 wrapped adjacent to the central pin 1110 and the metallic tube 1340 wrapped concentrically to the insulated wire 1330 and outside the insulated wire 1330. The insulated wire 1330 can be wrapped outside the metallic tube 1340. The top 1658 of the ferrite core 1320 can be formed integrally with the left and right sides 1652 and 1654, bottom 1660, and ferrite center 1664, or can be connected to the sides 1652 and 1654, bottom 1660, and ferrite center 1664 after the metallic tube 1340 and insulated wire 1330 have been wrapped around the ferrite center 1664. FIG. 19 shows an example top view of the ferrite core 1320 when assembled, and FIG. 20 shows a side view of an assembled example core 1320 with an opening 2002 for entry and/or exit of the metallic tube 1340 and/or insulated wire 1330.

The insulated wire 1330 and metallic tube 1340 can be wrapped directly around the ferrite center 1664, or may be wrapped around a bobbin 1620 inserted into the ferrite core 1320 over the ferrite center 1664.

When arranged in the inductive coil module assembly, an outflow portion of the metallic tube 1340 exiting the inductive coil module assembly 1200 can contact an inflow portion of the metallic tube 1340 entering the assembly 1200. For example, the outflow portion can be welded to the inflow portion, or the outflow and inflow portions can be wrapped together in a heat-shrink encasing. Alternatively, the outflow and inflow portions can pass through an opening into the box that is small enough to maintain contact between the outflow and inflow portions, without a physical connection between the outflow and inflow portions.

Figure 21:
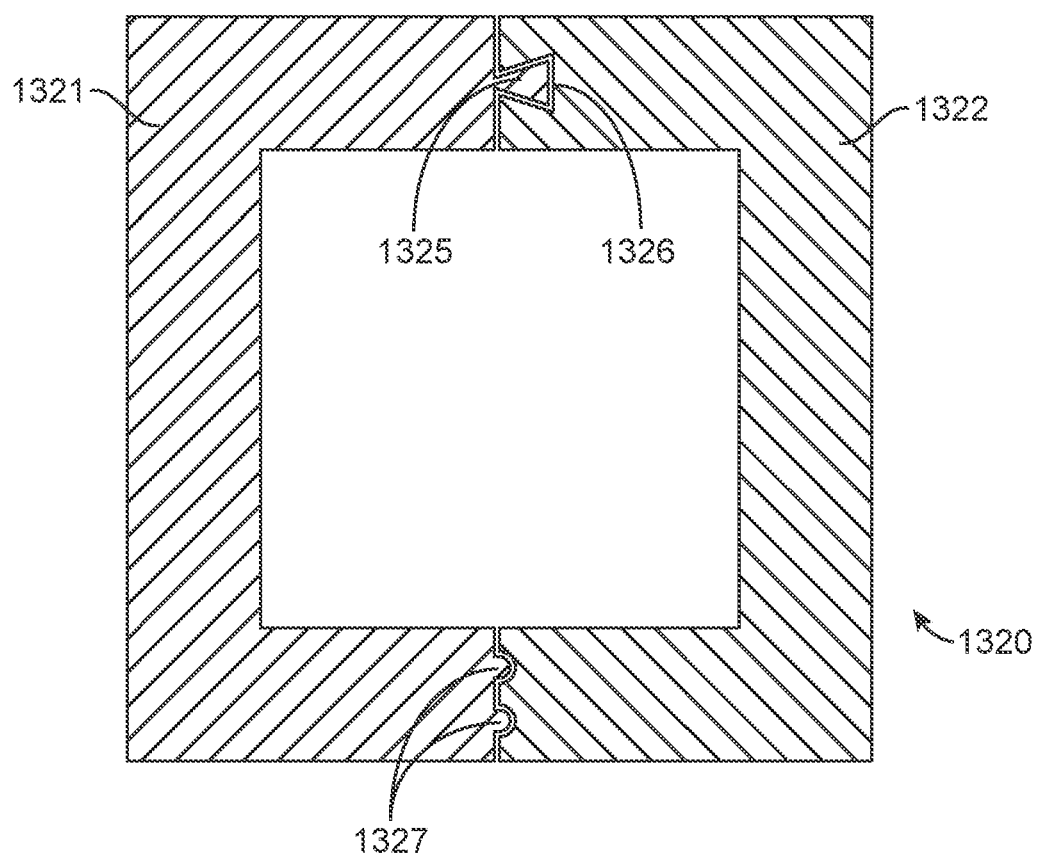
FIG. 21 illustrates in cross-section an example of attachment mechanisms facilitating assembly of a closed loop ferrite core.

As described above, the ferrite core 1320 can be assembled from multiple pieces 1321 and 1322 of ferrite core. FIG. 21 illustrates in cross-section an example of attachment mechanisms facilitating assembly of the ferrite core 1320. The attachment mechanism can include a tongue 1325 and groove 1326 configuration of mating surfaces of the ferrite core 1320 to facilitate mechanical attachment. Tongue 1325 protrusions can enter and mate with groove 1326 surfaces to align and connect the mating ferrite core surfaces. The attaching mechanism can include or use alternatively mechanical detents 1327 that can facilitate mating and locking the ferrite pieces together.

In addition, the attachment mechanism can include male and female connections of the ferrite core 1320 mating surfaces that mechanically meet and contain mechanical detents to physically complete the magnetic field.

In addition, the attachment mechanism can include magnetic components that serve to align and mate the surfaces of the ferrite core pieces to complete the magnetic field within the induction coil assembly 1410. Mating magnetic connectors can also be used within a cartridge assembly to facilitate alignment and connection of the cartridge and the handle of the vapor delivery device.

In addition, the attachment mechanism can include screws and receiving grooves. Ferrite core pieces can be screwed together with mating pitch threads and receiving grooves that allow the multiple ferrite pieces to be assembled together to complete the magnetic field.

In addition, the attachment mechanism can include a bayonet configuration. The ferrite core pieces can be placed together, and mounted and locked together, by twisting or rotating the parts in relation to each other once a mounting piece has entered the receiving receptacle. As the twist occurs, the ramp within the receptacle can force the mating ferrite surfaces to complete the magnetic field.

Figure 22A:
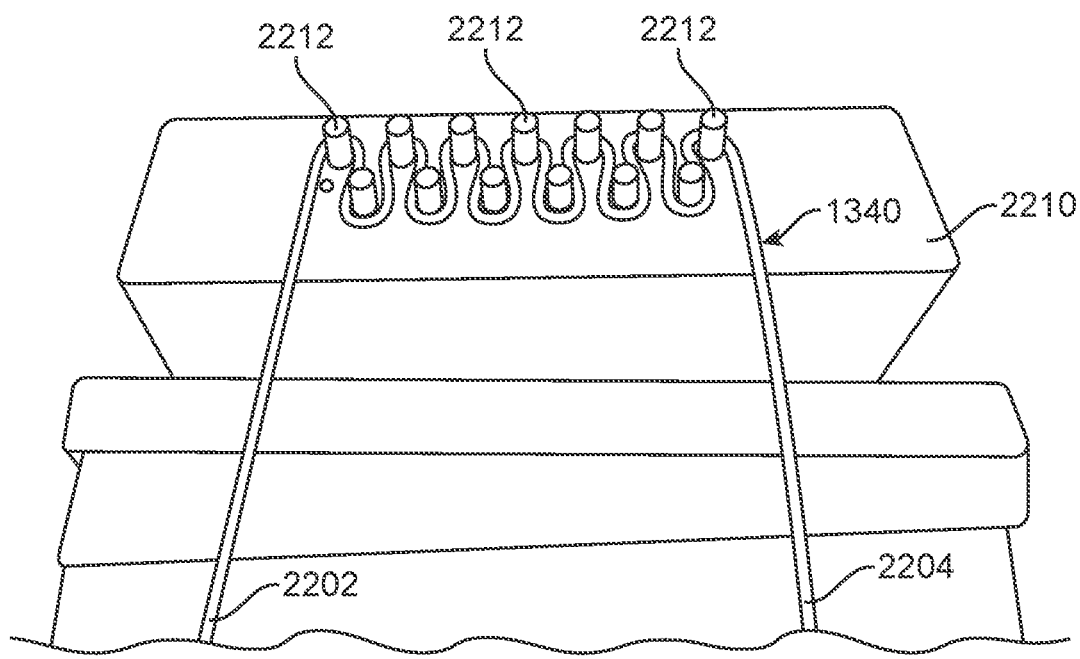
FIGS. 22A-22B illustrate example configurations of a metallic tube for heating fluid in a vapor delivery device.

FIG. 22A shows an example configuration of a metallic tube 1340 that can be used as a heating coil for heating fluid in the vapor delivery device. Metallic tube 1340 can have an input end 2202 and output end 2204 that are placed onto a fixture 2210. Metallic tube 1340 can be wrapped around pins 2212 on the fixture 2210 in a back and forth fashion. The number of wraps can be determined by the number of pins 2212.

Figure 22B:
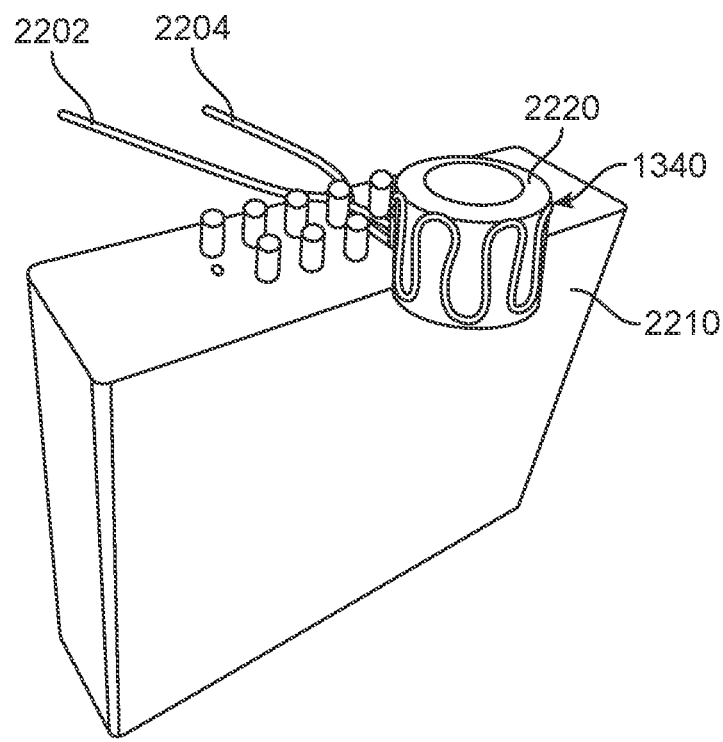

FIG. 22B shows the metallic tube 1340 with multiple wraps that can be placed in a circumferential configuration around a dielectric structure 2220. Output end 2204 and input end 2202 can be connectable to ports for fluid flow into the metallic tube 1340 and flow of heated fluid or vapor out of the metallic tube 1340. The axial wrapping configuration shown in FIG. 22B can advantageously extend the amount of time the fluid within the metallic tube 1340 can be exposed to heat for vapor production when this type of tube configuration is attached to an inductive coil assembly.

Metallic tube 1340 used for a fluid heating coil can be made from D-shaped tubing, rectangular or square tubing, or tubing with multiple twists in the coil. The metallic tubing 1340 can have varying diameters to increase or decrease fluid or vapor flow within the heating coil, and can have internal diameter restrictions that also serve to decrease or increase fluid or vapor flow.

Vapor Delivery Device with Detachable Cartridge Assembly

Figure 23:
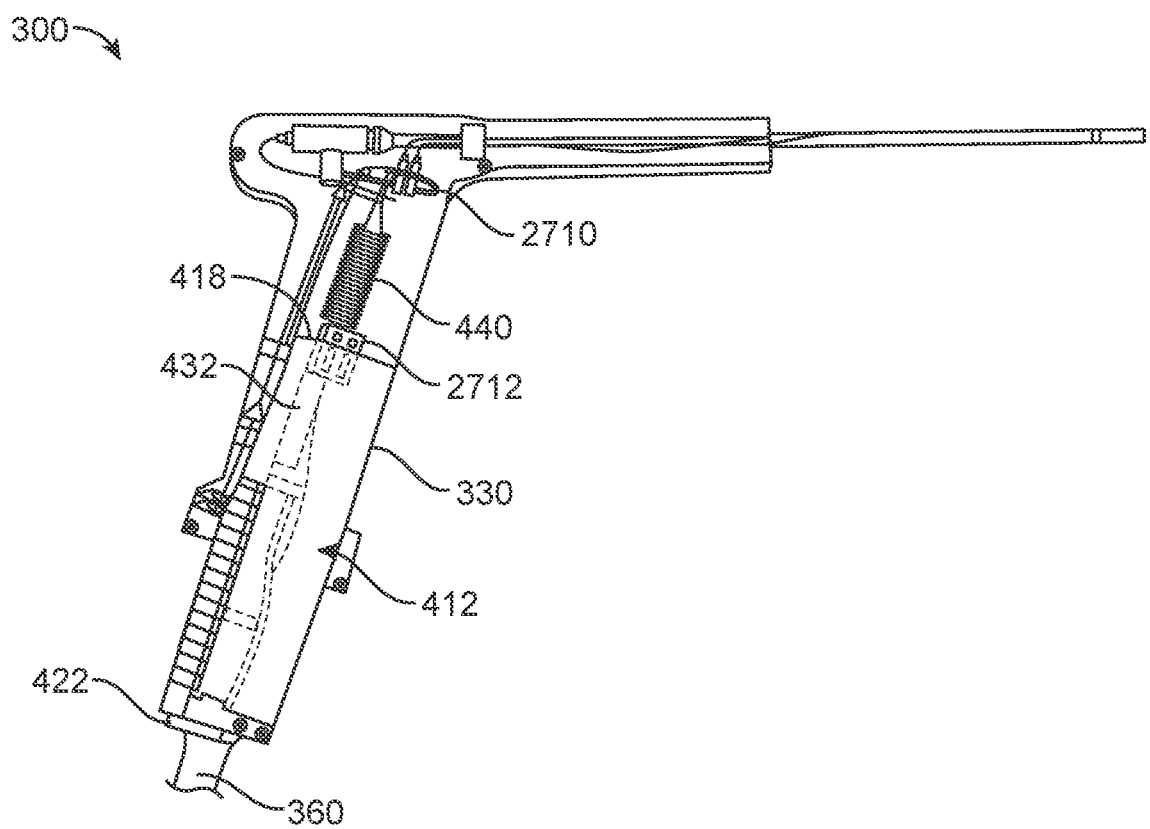
FIG. 23 illustrates an example vapor delivery device with a cartridge assembly.

FIG. 23 shows in cross-section an assembled vapor delivery device 300 can be detachably coupled to the cartridge assembly 412 by a tab lock, a push button lock, a spring actuated lock, mechanical detents, magnetic coupling, or a combination thereof. The cartridge assembly 412 can house the wound Litz wire 432 such that when the cartridge assembly 412 is extended into the proximal opening 422 of the handle 330, the metallic tube 440 (e.g., the heating coil) is slid through the induction coil opening 418 and into a lumen of the wound Litz wire 432 within the cartridge assembly 412. The cartridge assembly 412 can also be detached from the handle 330 of the vapor delivery device 300 and the metallic tube 440 can be slid out of the lumen of the wound Litz wire 432 and out of the induction coil opening 418.

Figure 24:
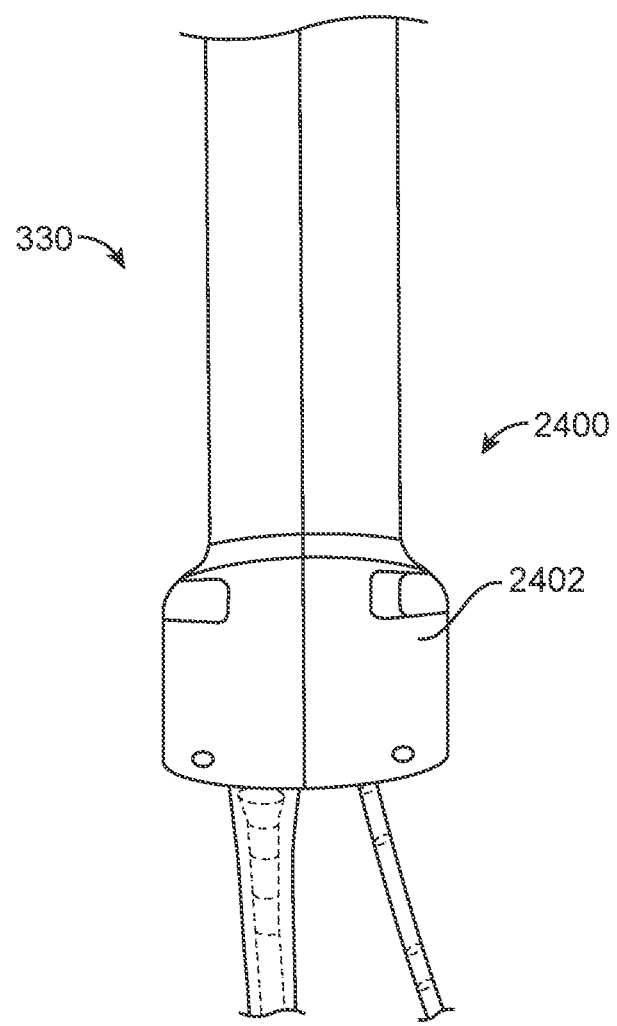
FIG. 24 illustrates an example lock tab for coupling a cartridge assembly to a vapor delivery device.
Figure 25:
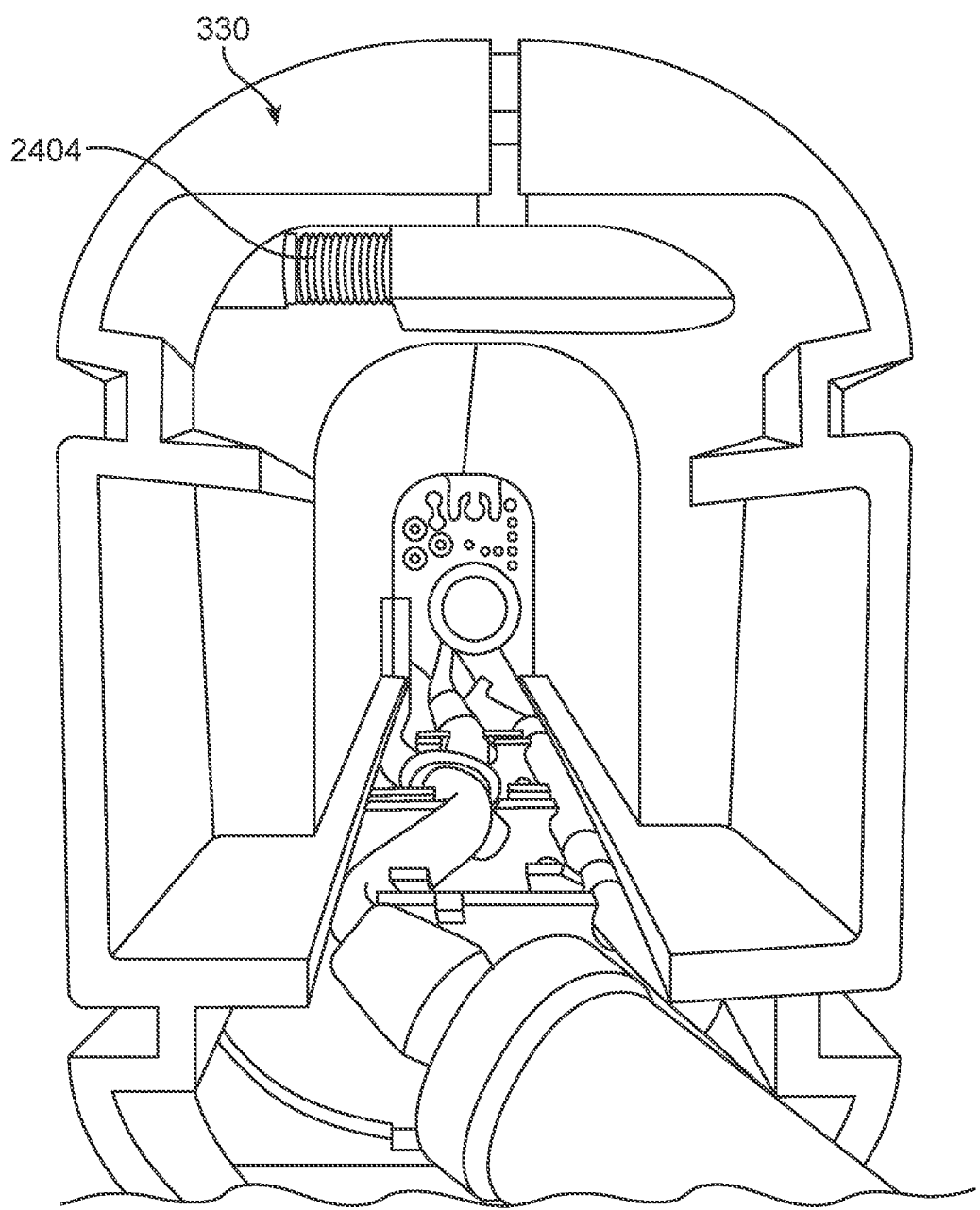
FIG. 25 illustrates an example lock tab for coupling a cartridge assembly to a vapor delivery device.
Figure 26:
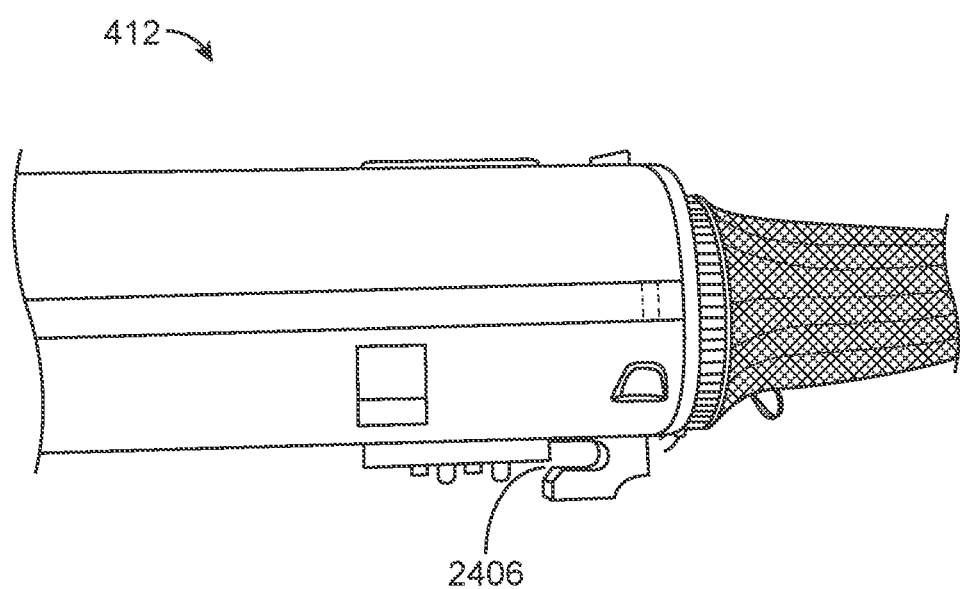
FIG. 26 illustrates a side view of a cartridge assembly.

FIGS. 24 and 25 illustrate that the handle 330 of the vapor delivery device 300 can be coupled to the cartridge assembly 412 by a lock tab 2400. The lock tab 2400 can have a push button 2402 that actuates a spring 2404 coupled to the push button 2402 shown in FIG. 25. The spring 2404 can fit within a slot or opening 2406 along a side of the cartridge assembly 412 shown in FIG. 26.

The cartridge assembly 412 can comprise a number of connectors, thermocouples, sensors, valves, or a combination thereof. For example, the sensors can include infrared (IR) sensors, intrauterine pressure sensor, or a combination thereof. Also, for example, the valves can be pneumatic valves. The connectors extending from the cartridge assembly can be male connectors. This allows the cartridge assembly 412 to be more easily sterilized. The connectors can also be female connectors having a removable cap or cover.

Figure 27:
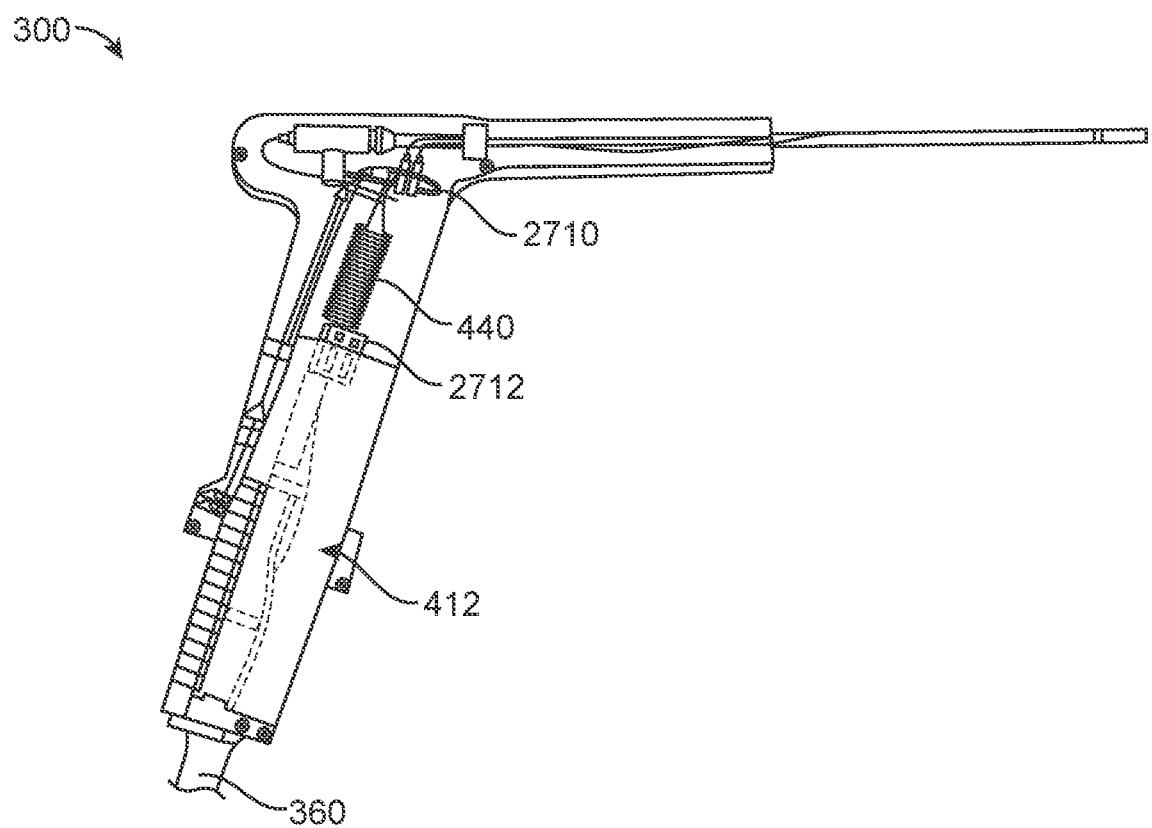
FIG. 27 illustrates a memory in an example vapor delivery device.

FIG. 27 illustrates that the handle 330 can include a non-volatile memory component such as an electrically erasable programmable read-only memory (EEPROM) 2710. The EEPROM 2710 can be housed within the handle housing. The EEPROM 2710 can be positioned above the metallic tube. FIG. 27 also illustrates that the cartridge assembly 412 can also one or more EEPROM controller leads 2712 coupled to a top of the cartridge assembly 412. The EEPROM controller leads 2712 can electrically couple with the EEPROM 2710 within the handle 330 when the cartridge assembly 412 is slid into a lumen of the handle 330 and detachably coupled to the handle 330 (e.g., via the lock tab mechanism 2400).

Figure 28:
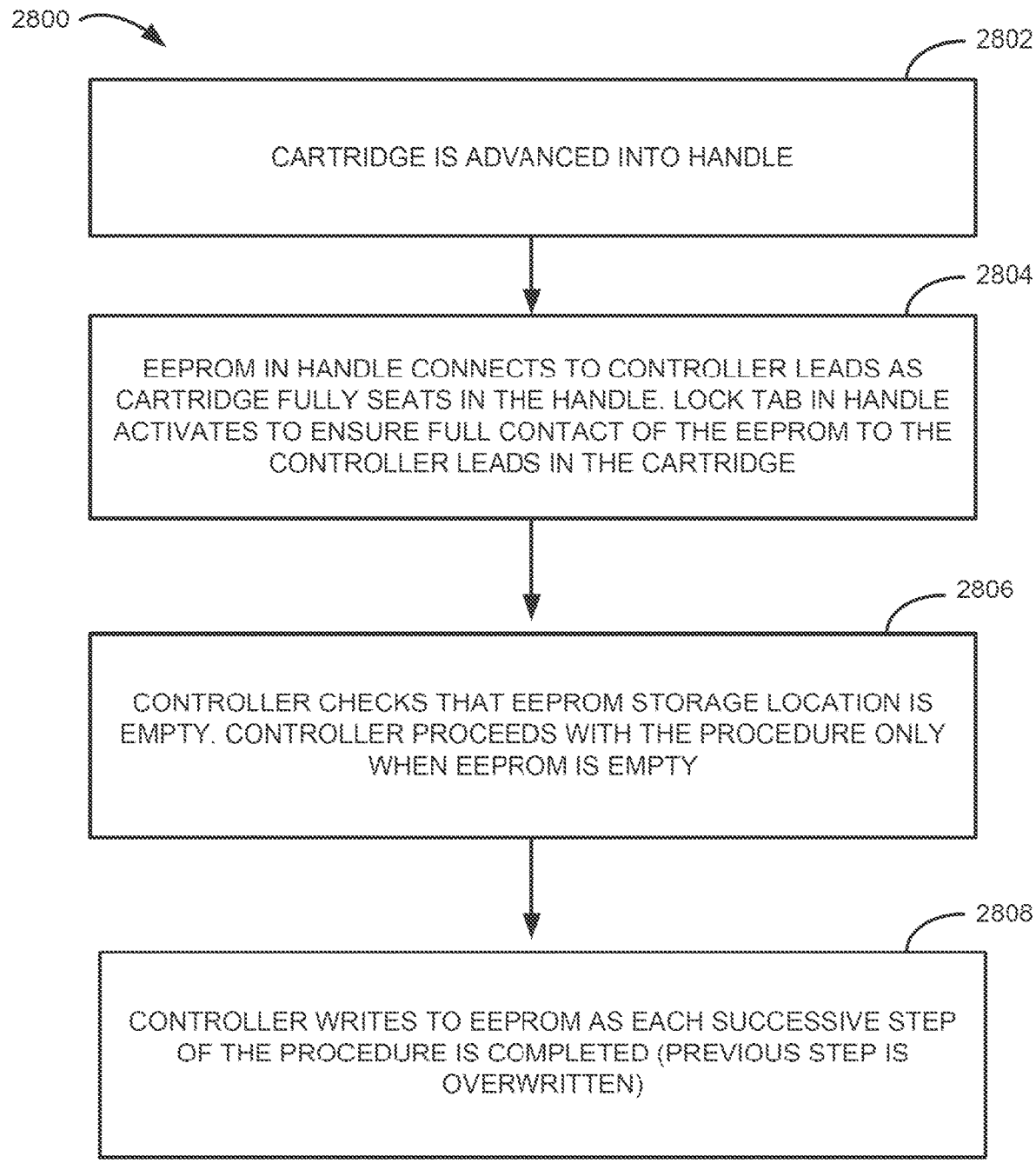
FIG. 28 illustrates an example cartridge control procedure.

FIG. 28 illustrates an example of a cartridge control procedure 2800. The procedure 2800 can involve advancing the cartridge assembly 412 into the handle 330 in step 2802. The procedure 2800 can also involve the EEPROM 2710 in the handle 330 connecting to the EEPROM controller leads 2712 as the cartridge assembly 412 is fully seated or is detachably coupled to the handle 330 (e.g., via the lock tab mechanism 2400). For example, the lock tab mechanism 5002 can be configured such that the EEPROM 2710 is in contact with the EEPROM controller leads 2712 when the lock tab mechanism 500 secures the cartridge assembly 412 to the inside of the handle 330. The procedure 2800 can also involve the controller checking to make sure that the EEPROM storage location is empty in step 2806. Step 2806 can also involve the controller proceeding with subsequent steps of the procedure 2800 when the EEPROM storage location is empty. If the EEPROM storage location is empty, the controller writes to the EEPROM 2710 in step 2808 as each successive step of the procedure is completed (e.g., as the previous step is overwritten). The cartridge control procedure 2800 can ensure that the controller is aware each time the cartridge assembly 412 is coupled to the handle 330. The cartridge control procedure 2800 also allows the controller to know which step of the treatment process has been undertaken by the vapor delivery device with a specific cartridge assembly 412 (based on the connection of the EEPROM 2710 in the handle 330 with the EEPROM controller leads 2712 on the cartridge assembly 412).

Damping Pressure Fluctuations

As described above, pressure in a bodily cavity can fluctuate during treatment with the vapor delivery device. For example, intrauterine pressure may be regulated to fall within a range between approximately 48 mmHg and 52 mmHg. To dampen the fluctuations of the intrauterine pressure curve and the vapor that exits the induction coil assembly and prior to exiting the vapor delivery device, an output end of the vapor delivery device can contain an additional compliant member that is shaped as a balloon, tubing, or separate compliant chamber that vapor initially enters the compliant chamber prior to exiting the vapor delivery device and into the uterine cavity.

Figure 29:
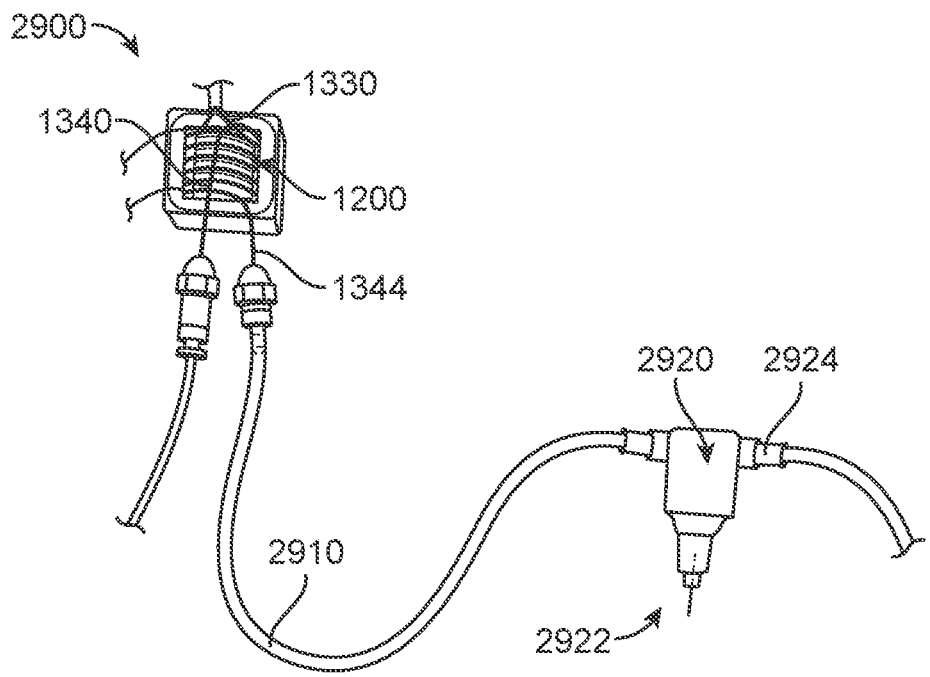
FIG. 29 illustrates an example system for damping pressure fluctuations.

FIG. 29 illustrates an example system 2900 for damping pressure fluctuations. The system 2900 can include an induction coil assembly 1200 with a metallic fluid tube 1340 and a Litz wire 1330. Coupled to the outflow portion 1344 of the metallic tube 1340 can be a compliant member 2910 and a chamber 2920. Heated or vaporized fluid can pass through the compliant member 2910 and chamber 2920 before reaching a patient.

The compliant member 2910 can be made from silicone or other elastomeric material that can withstand vapor temperatures. The compliant member 2910 can be shaped like a tube or balloon that can expand upon exposure to vapor pressures. The compliance of the compliant member 2910 provided to the vapor exiting the induction coil, and prior to exiting the vapor delivery device and the entering the uterine cavity, can reduce or damp the fluctuations of vapor pressure that is provided to the uterine cavity.

The complaint chamber 2920 can be a separate compartment or container for vapor that can contain an exit regulator 2922 to control or govern the exit of vapor from the induction coil 1200 prior to exiting the vapor delivery device. The chamber 2920 can be a volume between approximately 5 mL and 60 mL, and can have an output 2924 for passing fluid to output channels of the vapor delivery device for delivery to a patient. Fluid exiting the induction coil assembly 1200 may be a mix of vapor and liquid. Because the liquid has a different viscosity than the vapor, the liquid can cause pressure swings as it passes through output channels of the vapor delivery device. As the vapor and heated liquid pass through the chamber 2920, the heavier liquid can fall towards the exit regulator 2922 while the vapor can pass through the chamber output port 2924. The fluid beyond the chamber output port 2924 may therefore have a higher vapor quality than fluid entering the chamber 2920. The chamber 2920 may additionally have compliant walls to further damp pressure variations.

Figure 30A:
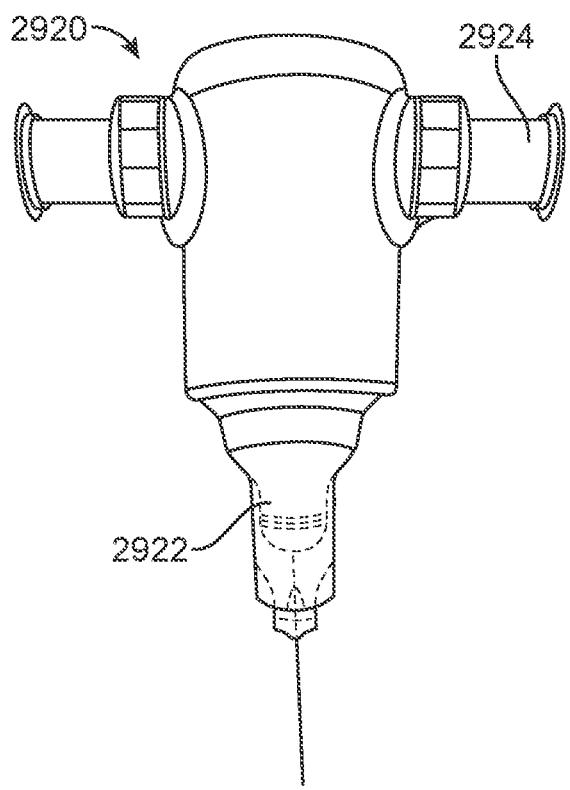
FIGS. 30A-30B illustrate example chambers for damping pressure fluctuations.
Figure 30B:
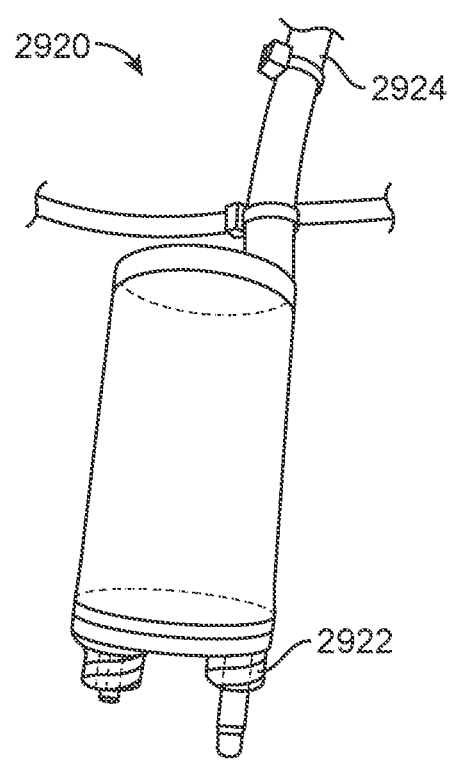

FIGS. 30A and 30B illustrate examples of the chamber 2920. The exit regulator 2922 can allow collected liquid to exit the chamber 2920. The exit regulator 2922 can be a flow restrictor allowing liquid to drain from the chamber 2920 at a specified rate. For example, the flow restrictor can be designed to drain liquid at approximately a rate at which the liquid is expected to collect in the chamber 2920. The exit regulator 2922 can alternatively comprise a valve that can be opened at periodic intervals to drain the collected liquid from the chamber 2920. The valve can open automatically at a specified pressure (e.g., when a specified volume of liquid has collected in the chamber 2920). The valve can alternatively be controlled pneumatically or electronically to open at a specified interval of time, or when a pressure sensor detects a specified pressure in the chamber 2920. An absorbent member can be placed in the chamber 2920 in addition to or instead of the exit regulator 2922.

As stated herein, the induction coil vapor generator can include a wrapping of Litz wire, insulated wire, or coiled magnet wire 102 which in this embodiment is supported by an outer assembly 104, and an inner assembly 106 disposed within the outer assembly. The induction coil 100 contains lumens, tubes, cavities, or metallic microtubes 108 disposed within the inner assembly 104. The tubes can be coupled to a fluid source 118 that supplies saline, water, distilled water, or other fluid that will be heated or converted into steam or vapor. In some embodiments, the outer assembly can comprise an electrically insulating and thermally insulating material, such as aerogel, foam, fiberglass, or low density silicone. To further provide insulation, the outer assembly can contain air gaps. The outer assembly can be thermally insulating to prevent heat from damaging the coiled magnet wire during the treatment cycle. Since the Litz wire or insulated wire can become excessively heated, the insulation is designed to prevent heat from engaging the patient or the operator. The excessive heat can also damage other medical device components in close proximity to the inductive coil. The inner assembly can comprise an electrically insulating, thermally conductive material, such as aluminum nitride, alloys of iron including stainless steels, alloys of nickel including ferrite, alloys of cobalt, quartz, glass, or a ceramic such as aluminum oxide. The inner assembly and the tubes contained within or in close proximity can be thermally conductive so as to inductively heat the fluid supplied by the fluid source 118. For the application of uterine endometrial ablation, the fluid is converted into vapor that can be delivered into the uterine cavity.

The Litz or insulated wire 102 can comprise any electrically insulated wire, such as insulated copper, silver, gold or aluminum wire used in electromagnets (magnet wire).

The device can have only one metallic tube that is formed and wrapped around the inner assembly. Having only one metallic tube can expose the fluid for a greater time duration within the heated inductive field and improves the vapor output of the assembly. The metallic tube can wrap around as a coil and can also be referred to as the "heating coil" in which fluid within the metallic tube is heated and converted to vapor.

The cartridge assembly 412 can contain no fluid pathways that deliver fluid or vapor to the patient which can further allow it to be a reusable component for cos savings purposes. The vapor delivery device 300 can contain the fluid conduit which threads through the handle and into the metallic tube, also called the heating coil. Fluid can be converted into vapor in the metallic tube once it is heated and provides vapor into the vapor input port which ultimately delivers the vapor to the uterine cavity through distal end. The vapor delivery device 300 can contain an intrauterine pressure sensor 451 located near the distal tip and sealing balloons 452 located in the position to interact with the endocervical canal once inserted within the patient.

The distal opening of the cartridge assembly can be positioned fully into the handle and the induction coil can be now fully assembled with insulated or Litz wire visible with heating coil or metallic tube. The physician can assemble the vapor delivery device 300 by inserting the cartridge assembly within the handle.

Monitoring for drops in intrauterine pressure, or rapid changes in vapor flow, may be incorporated into the software and hardware regulation system. For cervical seal failures, additional safety mechanisms such as thermocouples located in the cervix region can be utilized.

Vapor treatment (e.g., with shorter time durations than two minutes) can be used for small tumors, polyps, lungs, varicose veins, and smaller lumens, ducts, and bodily cavities.

The cartridge assembly's connector(s) can contain an inflow conduit and an outflow conduit, for example, to allow a flow of air to cool the inductive coil assembly.

As for additional details pertinent to the present disclosure, materials and manufacturing techniques may be employed as within the level of those with skill in the relevant art. The same may hold true with respect to method-based aspects of the disclosure in terms of additional acts commonly or logically employed. Also, it is contemplated that any optional feature of the variations described herein may be set forth and claimed independently, or in combination with any one or more of the features described herein. Likewise, reference to a singular item includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this disclosure belongs. The breadth of the present disclosure is not to be limited by the subject specification, but rather only by the plain meaning of the claim terms employed.

We claim:

1. An induction coil system, comprising:
   a coiled fluid tube configured to carry a fluid;
   a coiled wire configured to carry electric current, wherein the electric current in the coiled wire generates a magnetizing inductance to inductively heat the fluid tube;
   a capsule between the coiled fluid tube and the coiled wire; and
   a cooling fluid supply configured to force a cooling fluid through the capsule across the coiled wire.

2. The induction coil system of claim 1, wherein the capsule comprises a cooling fluid inlet port at a first end of the capsule and one or more cooling fluid outlet ports at a second end of the capsule, wherein the cooling fluid supply supplies the cooling fluid to the cooling fluid inlet port.

3. The induction coil system of claim 2, further comprising channels in an interior surface of the capsule extending from the first end to the second end.

4. The induction coil system of claim 3, wherein the channels are parallel to a central axis of the coiled wire.

5. The induction coil system of claim 3, wherein the coiled wire has a first length and the channels have a second length, wherein the second length is greater than or equal to the first length.

6. The induction coil system of claim 2, wherein the one or more cooling fluid outlet ports comprise a plurality of cooling fluid output ports at equal radii around the second end of the capsule and evenly angularly distributed around a longitudinal axis extending from the first end to the second end.

7. The induction coil system of claim 1, wherein the coiled wire comprises wire coiled around a ferrite core.

8. An induction coil system, comprising:
   a capsule comprising a cooling fluid inlet port and a cooling fluid outlet port;
   a coiled wire configured to carry electric current, wherein the coiled wire is at least partially enclosed within the capsule; and
   a cooling fluid supply configured to force a cooling fluid through the capsule from the cooling fluid inlet port to the cooling fluid outlet port.

9. The induction coil system of claim 8, further comprising channels in the capsule extending from a first end of the capsule to a second end of the capsule.

10. The induction coil system of claim 9, wherein the cooling fluid inlet port is positioned at the first end of the capsule and the cooling fluid outlet port is positioned at the second end of the capsule.

11. The induction coil system of claim 9, further comprising a plurality of cooling fluid outlet ports, wherein each of the channels directs the cooling fluid to one of the plurality of cooling fluid outlet ports.

12. The induction coil system of claim 9, wherein the channels are parallel to a central axis of the coiled wire.

13. The induction coil system of claim 9, wherein the coiled wire has a first length and the channels have a second length, and wherein the second length is greater than or equal to the first length.

14. The induction coil system of claim 11, wherein the plurality of cooling fluid outlet ports comprise a plurality of cooling fluid output ports at equal radii around the second end of the capsule and evenly angularly distributed around a longitudinal axis extending from a first end of the capsule to a second end of the capsule.

15. An induction coil system, comprising:
   a capsule comprising a cooling fluid inlet port at a first end of the capsule and a cooling fluid outlet port at a second end of the capsule;
   a fluid tube configured to carry a fluid, wherein the fluid tube is wrapped one or more times around an exterior of the capsule;
   a coiled wire configured to carry electric current, wherein the coiled wire is at least partially enclosed within the capsule and wherein the electric current in the coiled wire generates a magnetizing inductance to inductively heat the fluid tube; and
   a cooling fluid supply configured to force a cooling fluid through the capsule from the cooling fluid inlet port to the cooling fluid outlet port.

16. The induction coil system of claim 15, further comprising channels in an interior surface of the capsule extending from the first end to the second end.

17. The induction coil system of claim 16, wherein the channels are parallel to a central axis of the coiled wire.

18. The induction coil system of claim 16, wherein the coiled wire has a first length and the channels have a second length, wherein the second length is greater than or equal to the first length.

19. The induction coil system of claim 15, further comprising a plurality of cooling fluid outlet ports at equal radii around the second end of the capsule and evenly angularly distributed around a longitudinal axis extending from the first end to the second end.

20. The induction coil system of claim 15, wherein the fluid tube when wrapped the one or more times around the exterior of the capsule is concentric to and at least partially overlapping the coiled wire.

* * * * *